US012747279B2

(12) United States Patent
Yao et al.

(10) Patent No.: US 12,747,279 B2
(45) Date of Patent: *Sep. 29, 2026

(54) CONSTRUCTION OF CHIMERIC ANTIGEN RECEPTOR TARGETING CD20 ANTIGEN AND ACTIVITY IDENTIFICATION OF ENGINEERED T CELLS THEREOF

(71) Applicant: AbelZeta Inc., Rockville, MD (US)

(72) Inventors: Yihong Yao, Rockville, MD (US); Jiaqi Huang, Rockville, MD (US); Shigui Zhu, Rockville, MD (US); Wei Zhu, Rockville, MD (US); Xin Yao, Rockville, MD (US); Zhiyuan Li, Shanghai (CN); Li Zhang, Rockville, MD (US); Lin Zhu, Shanghai (CN); Anyun Ma, Shanghai (CN); Yutian Wei, Shanghai (CN); Yanfeng Li, Shanghai (CN); Qingxia Wang, Shanghai (CN); Jiaping He, Shanghai (CN)

(73) Assignee: AbelZeta Inc., Rockville, MD (US)

( * ) Notice: Subject to any disclaimer, the term of this patent is extended or adjusted under 35 U.S.C. 154(b) by 785 days.

This patent is subject to a terminal disclaimer.

(21) Appl. No.: 18/173,187

(22) Filed: Feb. 23, 2023

(65) Prior Publication Data

US 2023/0242613 A1 Aug. 3, 2023

Related U.S. Application Data

(63) Continuation of application No. 17/723,859, filed on Apr. 19, 2022, now Pat. No. 11,618,778, which is a continuation of application No. 17/352,915, filed on Jun. 21, 2021, now Pat. No. 11,472,858, which is a continuation of application No. 16/484,482, filed as (Continued)

(30) Foreign Application Priority Data

Feb. 8, 2017 (CN) ........................ 201710069569.7

(51) Int. Cl.

| | |
|---|---|
| ***C07K 14/725*** | (2006.01) |
| ***A61K 9/00*** | (2006.01) |
| ***A61K 35/17*** | (2025.01) |
| ***A61K 38/00*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***A61P 35/02*** | (2006.01) |
| ***C07K 14/705*** | (2006.01) |
| ***C07K 16/28*** | (2006.01) |
| ***C07K 19/00*** | (2006.01) |
| ***C12N 5/0783*** | (2010.01) |
| ***C12N 5/10*** | (2006.01) |
| ***C12N 7/00*** | (2006.01) |
| ***C12N 15/62*** | (2006.01) |
| ***C12N 15/86*** | (2006.01) |

(52) U.S. Cl.

CPC ........ *C07K 14/7051* (2013.01); *A61K 9/0019* (2013.01); *A61K 40/11* (2025.01); *A61K 40/31* (2025.01); *A61K 40/4221* (2025.01); *A61P 35/00* (2018.01); *A61P 35/02* (2018.01); *C07K 14/70517* (2013.01); *C07K 14/70521* (2013.01); *C07K 14/70578* (2013.01); *C07K 16/2887* (2013.01); *C07K 19/00* (2013.01); *C12N 5/0636* (2013.01); *C12N 5/10* (2013.01); *C12N 7/00* (2013.01); *C12N 15/62* (2013.01); *C12N 15/86* (2013.01); *A61K 38/00* (2013.01); *A61K 2039/505* (2013.01); *A61K 2039/54* (2013.01); *C07K 2317/524* (2013.01); *C07K 2317/526* (2013.01); *C07K 2317/53* (2013.01); *C07K 2317/622* (2013.01); *C07K 2317/732* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2740/15043* (2013.01); *C12N 2750/14143* (2013.01)

(58) Field of Classification Search

None

See application file for complete search history.

(56) References Cited

U.S. PATENT DOCUMENTS 6,074,841 A 6/2000 Gearing et al.
6,410,319 B1 6/2002 Raubitschek et al.
(Continued)

FOREIGN PATENT DOCUMENTS

CN 101544694 A 9/2009
CN 106279434 A 1/2017
(Continued)

OTHER PUBLICATIONS

US 11,419,896 B2, 08/2022, Yao et al. (withdrawn)
(Continued)

*Primary Examiner* — Robert M Kelly

(74) *Attorney, Agent, or Firm* — LEASON ELLIS LLP

(57) ABSTRACT

Provided are a chimeric antigen receptor targeting CD20 antigen and a preparation method thereof. The extracellular antigen binding domain of the chimeric antigen receptor includes an antibody heavy chain variable region shown in SEQ ID NO: 7 or 9 or 33 and an antibody light chain variable region shown in SEQ ID NO: 11 or 13 or 35, and is capable of killing tumor cells.

9 Claims, 9 Drawing Sheets

Specification includes a Sequence Listing.

Related U.S. Application Data application No. PCT/CN2018/075867 on Feb. 8, 2018, now Pat. No. 11,066,457.

(56) References Cited

U.S. PATENT DOCUMENTS

| | | | |
|---|---|---|---|
| 7,446,179 | B2 | 11/2008 | Jensen et al. |
| 7,446,190 | B2 | 11/2008 | Sadelain et al. |
| 7,462,352 | B2 | 12/2008 | Hansen et al. |
| 8,287,864 | B2 | 10/2012 | Goldenberg et al. |
| 8,329,181 | B2 | 12/2012 | Martin et al. |
| 8,389,282 | B2 | 3/2013 | Sadelain et al. |
| 8,399,645 | B2 | 3/2013 | Campana et al. |
| 8,529,902 | B2 | 9/2013 | Teeling et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,328,156 | B2 | 5/2016 | June et al. |
| 9,447,194 | B2 | 9/2016 | Jensen |
| 9,464,140 | B2 | 10/2016 | June et al. |
| 9,481,728 | B2 | 11/2016 | June et al. |
| 9,499,629 | B2 | 11/2016 | June et al. |
| 9,518,123 | B2 | 12/2016 | June et al. |
| 9,540,445 | B2 | 1/2017 | June et al. |
| 9,605,049 | B2 | 3/2017 | Campana et al. |
| 9,662,354 | B2 | 5/2017 | Hyde et al. |
| 9,834,590 | B2 | 12/2017 | Campana et al. |
| 9,856,322 | B2 | 1/2018 | Campana et al. |
| 9,919,061 | B2 | 3/2018 | McDonagh et al. |
| 10,040,827 | B2 | 8/2018 | Delecluse et al. |
| 10,189,903 | B2 | 1/2019 | Jensen |
| 10,221,245 | B2 | 3/2019 | Brogdon et al. |
| 10,287,350 | B2 | 5/2019 | Kochenderfer |
| 10,442,867 | B2 | 10/2019 | Orentas et al. |
| 10,457,730 | B2 | 10/2019 | Pule et al. |
| 10,493,139 | B2 | 12/2019 | Wu et al. |
| 10,501,539 | B2 | 12/2019 | Schneider et al. |
| 10,507,219 | B2 | 12/2019 | Gilbert |
| 10,525,083 | B2 | 1/2020 | Brannetti et al. |
| 10,533,055 | B2 | 1/2020 | Chen et al. |
| 10,603,380 | B2 | 3/2020 | Wilzius |
| 10,639,329 | B2 * | 5/2020 | Dropulic .............. A61K 40/428 |
| 10,736,918 | B2 | 8/2020 | Jensen et al. |
| 11,026,976 | B2 | 6/2021 | Brannetti et al. |
| 11,066,457 | B2 | 7/2021 | Yao et al. |
| 11,207,349 | B2 | 12/2021 | Yao et al. |
| 11,439,665 | B2 | 9/2022 | Yao et al. |
| 11,472,858 | B2 | 10/2022 | Yao et al. |
| 11,608,369 | B2 | 3/2023 | Yao et al. |
| 11,618,778 | B2 | 4/2023 | Yao et al. |
| 11,633,430 | B2 | 4/2023 | Yao et al. |
| 11,890,300 | B2 | 2/2024 | Lock et al. |
| 11,890,301 | B2 | 2/2024 | June et al. |
| 12,458,667 | B2 | 11/2025 | Yao et al. |
| 2004/0167319 | A1 | 8/2004 | Teeling |
| 2009/0148447 | A1 | 6/2009 | Ledbetter |
| 2011/0091473 | A1 | 4/2011 | Golab |
| 2013/0004480 | A1 | 1/2013 | Parren |
| 2013/0224205 | A1 | 8/2013 | Hofmeister |
| 2014/0093454 | A1 | 4/2014 | Teeling et al. |
| 2014/0154253 | A1 | 6/2014 | Ng |
| 2015/0038684 | A1 | 2/2015 | Jensen |
| 2015/0306141 | A1 | 10/2015 | Jensen et al. |
| 2016/0145337 | A1 | 5/2016 | Galetto et al. |
| 2016/0152723 | A1 | 6/2016 | Chen et al. |
| 2016/0158359 | A1 | 6/2016 | Gilbert |
| 2016/0333108 | A1 | 11/2016 | Forman |
| 2016/0362472 | A1 | 12/2016 | Bitter |
| 2017/0073664 | A1 | 3/2017 | McCafferty et al. |
| 2017/0267756 | A1 | 9/2017 | Riddell et al. |
| 2017/0275382 | A1 | 9/2017 | Poma |
| 2017/0355767 | A1 | 12/2017 | Engelberts et al. |
| 2017/0368098 | A1 | 12/2017 | Chen |
| 2018/0044415 | A1 | 2/2018 | Escarpe |
| 2018/0044417 | A1 | 2/2018 | Pule et al. |
| 2018/0085401 | A1 | 3/2018 | Wu et al. |
| 2018/0118823 | A1 | 5/2018 | Thompson |
| 2018/0125892 | A1 | 5/2018 | Brannetti |
| 2018/0142034 | A1 | 5/2018 | Chang |
| 2018/0142035 | A1 | 5/2018 | Lobb |
| 2018/0153977 | A1 | 6/2018 | Wu et al. |
| 2018/0230225 | A1 | 8/2018 | Fan |
| 2018/0243341 | A1 | 8/2018 | June et al. |
| 2018/0258391 | A1 | 9/2018 | June et al. |
| 2018/0265585 | A1 | 9/2018 | Kong |
| 2018/0312588 | A1 | 11/2018 | Wilzius et al. |
| 2018/0319862 | A1 | 11/2018 | Thompson et al. |
| 2018/0355052 | A1 | 12/2018 | Orentas et al. |
| 2018/0355318 | A1 | 12/2018 | Delaney et al. |
| 2019/0106501 | A1 | 4/2019 | Press |
| 2019/0107537 | A1 | 4/2019 | Chaudhary |
| 2019/0112380 | A1 | 4/2019 | Chaudhary |
| 2019/0119382 | A1 | 4/2019 | Jensen |
| 2019/0135940 | A1 | 5/2019 | Brogdon et al. |
| 2019/0144515 | A1 | 5/2019 | Sievers et al. |
| 2019/0169289 | A1 | 6/2019 | Young et al. |
| 2019/0321404 | A1 | 10/2019 | Fan et al. |
| 2020/0002400 | A1 | 1/2020 | Yao et al. |
| 2020/0040096 | A1 | 2/2020 | Forman et al. |
| 2020/0078405 | A1 | 3/2020 | Jensen et al. |
| 2020/0093861 | A1 | 3/2020 | Klein et al. |
| 2020/0109210 | A1 | 4/2020 | Orentas et al. |
| 2020/0215108 | A1 | 7/2020 | Jensen |
| 2020/0216534 | A1 | 7/2020 | Davila |
| 2020/0246382 | A1 | 8/2020 | Perez et al. |
| 2020/0289517 | A1 | 9/2020 | He |
| 2020/0306375 | A1 | 10/2020 | Lobb et al. |
| 2020/0308223 | A1 | 10/2020 | Chang |
| 2021/0079111 | A1 | 3/2021 | Zhang et al. |
| 2021/0290673 | A1 | 9/2021 | Yao |
| 2021/0363245 | A1 | 11/2021 | Kochenderfer et al. |
| 2021/0388100 | A1 | 12/2021 | Satpayev et al. |
| 2022/0249568 | A1 | 8/2022 | Yao et al. |
| 2022/0281945 | A1 | 9/2022 | Yao et al. |
| 2022/0340640 | A1 | 10/2022 | Yao et al. |
| 2023/0036065 | A1 | 2/2023 | McCreedy, Jr. et al. |
| 2023/0104705 | A1 | 4/2023 | Yao et al. |
| 2023/0212255 | A1 | 7/2023 | Yao et al. |
| 2024/0034802 | A1 | 2/2024 | Orentas et al. |
| 2024/0115605 | A1 | 4/2024 | Yao et al. |
| 2024/0139243 | A1 | 5/2024 | Yao et al. |
| 2025/0144144 | A1 | 5/2025 | Chen et al. |
| 2025/0262243 | A1 | 8/2025 | Yao et al. |

FOREIGN PATENT DOCUMENTS

| | | | |
|---|---|---|---|
| CN | 107868791 | A | 4/2018 |
| CN | 107936120 | A | 4/2018 |
| CN | 108017717 | A | 5/2018 |
| CN | 108285486 | A | 7/2018 |
| CN | 108395482 | A | 8/2018 |
| CN | 108472346 | A | 8/2018 |
| CN | 108715616 | A | 10/2018 |
| CN | 109423495 | A | 3/2019 |
| CN | 109536455 | A | 3/2019 |
| CN | 109575143 | A | 4/2019 |
| CN | 110062768 | A | 7/2019 |
| CN | 110606893 | A | 12/2019 |
| CN | 110845623 | A | 2/2020 |
| CN | 112390891 | A | 2/2021 |
| CN | 112608387 | A | 4/2021 |
| EP | 3989986 | A1 | 5/2022 |
| JP | 2015-092865 | A | 5/2015 |
| JP | 2018-508215 | A | 3/2018 |
| WO | 00/23573 | A2 | 4/2000 |
| WO | 2012/079000 | A1 | 6/2012 |
| WO | 2013/123061 | A1 | 8/2013 |
| WO | 2014/012085 | A2 | 1/2014 |
| WO | 2016/014576 | A1 | 1/2016 |
| WO | 2016/097231 | A2 | 6/2016 |
| WO | 2016/100232 | A1 | 6/2016 |

(56) References Cited

FOREIGN PATENT DOCUMENTS

| | | | |
|---|---|---|---|
| WO | 2016/120216 | A1 | 8/2016 |
| WO | 2016/126608 | A1 | 8/2016 |
| WO | 2016/139487 | A1 | 9/2016 |
| WO | 2016/164731 | A2 | 10/2016 |
| WO | 2016/166521 | A1 | 10/2016 |
| WO | 2016/179319 | A1 | 11/2016 |
| WO | 2016/201394 | A1 | 12/2016 |
| WO | 2017/025038 | A1 | 2/2017 |
| WO | 2017/149515 | A1 | 9/2017 |
| WO | 2018/067992 | A1 | 4/2018 |
| WO | 2018/068766 | A1 | 4/2018 |
| WO | 2018/121604 | A1 | 7/2018 |
| WO | 2018/145649 | A1 | 8/2018 |
| WO | 2019/028051 | A1 | 2/2019 |
| WO | 2019/075395 | A1 | 4/2019 |
| WO | 2019/126724 | A1 | 6/2019 |
| WO | 2019/128952 | A1 | 7/2019 |
| WO | 2019/129177 | A1 | 7/2019 |
| WO | 2019/154313 | A1 | 8/2019 |
| WO | 2019/178576 | A1 | 9/2019 |
| WO | 2019/206326 | A1 | 10/2019 |
| WO | 2019/210153 | A1 | 10/2019 |
| WO | 2019/223226 | A1 | 11/2019 |
| WO | 2019/232444 | A1 | 12/2019 |
| WO | 2020/010235 | A1 | 1/2020 |
| WO | 2020/033273 | A1 | 2/2020 |
| WO | 2020/061796 | A1 | 4/2020 |
| WO | 2020/072536 | A1 | 4/2020 |
| WO | 2020/151752 | A1 | 7/2020 |
| WO | 2020/210665 | A1 | 10/2020 |
| WO | 2021/188681 | A1 | 9/2021 |

OTHER PUBLICATIONS

Edwards, et al. (2003) "The Remarkable Flexibility for the Human Antibody Repertoire; Isolation of Over One Thousand Different Antibodies to a Single Protein, BLyS" Journal of Molecular Biology, 334: 103-118. (Year: 2003).*

Goel, et al. (2004) "Plasticity within the Antigen-Combining Site May Manifest as Molecular Mimicry in the Humoral Immune Response", The Journal of Immunology, 173: 7358-67. (Year: 2004).*

Sadelain, et al. (2013) "The Basic Principles of Chimeric Antigen Design", Cancer Discovery, 3(4): 388-98 (Year: 2013).*

Dudek, et al. (2013) "Mitochondrial protein import: Common principles and physiological networks", Biochimica et Biophysica Acta, 1833: 274-85 (Year: 2013).*

Kosugi, et al. (2009) "Six Classes of Nuclear Localization Signals Specific to Different Binding Grooves of Importin α", The Journal of Biological Chemistry, 284(1): 478-85. (Year: 2009).*

Zhang, et al. (2016) "Treatment of CD20-directed Chimeric Antigen Receptor-modified T cells in patients with relapsed or refractory B-cell non-hodgkin lymphoma: an early phase IIa trial report", Signal Transduction and Targeted Therapy, 1: Article 16002, 9 pages. (Year: 2016).*

Buhler et al., Influence of structural variations on biological activity of anti-PSMA scFv and immunotoxins targeting prostate cancer. Anticancer Res. Sep. 2010;30(9):3373-9.

Chavez et al., CAR T-cell therapy for B-cell lymphomas: clinical trial results of available products. Ther Adv Hematol. Apr. 15, 2019;10:2040620719841581, 20 pages.

Dondelinger et al., Understanding the Significance and Implications of Antibody Numbering and Antigen-Binding Surface/Residue Definition. Front Immunol. Oct. 16, 2018;9:2278, 15 pages.

Du et al., Structure of the Fab fragment of therapeutic antibody Ofatumumab provides insights into the recognition mechanism with CD20. Mol Immunol. Jul. 2009;46(11-12):2419-23.

GenBank Accession No. AMZ04821.1, bi-specific chimeric antigen receptor 20-19 Short, partial [synthetic construct]. 1 page, Apr. 24, 2016.

GenBank Accession No. KX000911, Synthetic construct bi-specific chimeric antigen receptor (EAAAK)3 20-19 Short gene, partial cds. 2 pages, Apr. 24, 2016.

Ghafouri et al., CD19/CD20 bispecific chimeric antigen receptor (CAR) in naive/memory T-cells for the treatment of relapsed or refractory B-cell lymphomas. Jul. 1, 2021;81(13):Abstract CT007.

Kim et al., Improving the productivity of single-chain Fv antibody against c-Met by rearranging the order of its variable domains. J Microbiol Biotechnol. Jun. 2008;18(6):1186-90.

Kipriyanov et al., Effect of domain order on the activity of bacterially produced bispecific single-chain Fv antibodies. J Mol Biol. Jun. 27, 2003;330(1):99-111.

Kunik et al., Structural consensus among antibodies defines the antigen binding site. PLoS Comput Biol. 2012;8(2):e1002388.

Kussie et al., A single engineered amino acid substitution changes antibody fine specificity. J Immunol. Jan. 1, 1994;152(1):146-52.

Liang et al., Safety and efficacy of a novel anti-CD20/CD19 bi-specific CAR T-cell therapy (C-CAR039) in relapsed or refractory (r/r) B-cell non-Hodgkin lymphoma (B-NHL). Journal of Clinical Oncology. May 20, 2021;39(15 Suppl.):2 pages, Abstract 2507.

Liu et al., Fine mapping of the antigen-antibody interaction of scFv215, a recombinant antibody inhibiting RNA polymerase II from *Drosophila melanogaster*. J Mol Recognit. Mar.-Apr. 1999;12(2):103-11.

Makita et al., Clinical development of anti-CD19 chimeric antigen receptor T-cell therapy for B-cell non-Hodgkin lymphoma. Cancer Sci. Jun. 2017;108(6):1109-1118.

Martyniszyn et al., CD20-CD19 Bispecific CAR T Cells for the Treatment of B-Cell Malignancies. Hum Gene Ther. Dec. 2017;28(12):1147-1157.

Panka et al., Variable region framework differences result in decreased or increased affinity of variant anti-digoxin antibodies. Proc Natl Acad Sci U S A. May 1988;85(9):3080-4.

Rudikoff et al., Single amino acid substitution altering antigen-binding specificity. Proc Natl Acad Sci U S A. Mar. 1982;79(6):1979-83.

Schneider et al., A tandem CD19/CD20 CAR lentiviral vector drives on-target and off-target antigen modulation in leukemia cell lines. Journal for ImmunoTherapy of Cancer. 2017;5:42, 17 pages.

Sela-Culang et al., The structural basis of antibody-antigen recognition. Front Immunol. Oct. 8, 2013;4:302.

Shah et al., Bispecific anti-CD20, anti-CD19 CAR T cells for relapsed B cell malignancies: a phase 1 dose escalation and expansion trial. Nat Med. Oct. 2020;26(10):1569-1575.

Tong et al., Optimized tandem CD19/CD20 CAR-engineered T cells in refractory/relapsed B-cell lymphoma. Blood. Oct. 1, 2020;136(14):1632-1644.

Wark et al., Latest technologies for the enhancement of antibody affinity. Adv Drug Deliv Rev. Aug. 7, 2006;58 (5-6):657-70.

Watanabe et al., Target antigen density governs the efficacy of anti-CD20-CD28-CD3 ? chimeric antigen receptor-modified effector CD8+ T cells. J Immunol. Feb. 1, 2015;194(3):911-20.

Wong et al., Structural requirements for a specificity switch and for maintenance of affinity using mutational analysis of a phage-displayed anti-arsonate antibody of Fab heavy chain first complementarity-determining region. J Immunol. Jun. 15, 1998;160(12):5990-7.

Zah et al., Addendum: T Cells Expressing CD19/CD20 Bispecific Chimeric Antigen Receptors Prevent Antigen Escape by Malignant B Cells. Cancer Immunol Res. Jul. 2016;4(7):639-41.

Zah et al., T Cells Expressing CD19/CD20 Bispecific Chimeric Antigen Receptors Prevent Antigen Escape by Malignant B Cells. Cancer Immunol Res. Jun. 2016;4(6):498-508.

Zhou et al., The efficacy and safety of anti-CD19/CD20 chimeric antigen receptor-T cells immunotherapy in relapsed or refractory B-cell malignancies:a meta-analysis. BMC Cancer. Sep. 26, 2018;18(1):929, 13 pages.

Zhu et al., Closed-system manufacturing of CD19 and dual-targeted CD20/19 chimeric antigen receptor T cells using the CliniMACS Prodigy device at an academic medical center. Cytotherapy. Mar. 2018;20(3):394-406.

International Search Report and Written Opinion for Application No. PCT/US2021/022779, dated Aug. 9, 2021, 16 pages.

(56) References Cited

OTHER PUBLICATIONS

International Search Report and Written Opinion for Application No. PCT/CN2020/109645, dated Dec. 16, 2020, 15 pages.
Rufener, Gregory A. et al., "Preserved Activity of CD20-Specific Chimeric Antigen Receptor-A Expressing T Cells in the Presence of Rituximab" Cancer Immunology Research, 4(6), Jun. 2016, pp. 509-519.
Wang, D. et al., "GenBank Accession No. AKH40187, Version AKH40187.1" GenBank, Jul. 28, 2015.
International Search Report/Written Opinion mailed May 9, 2018 for PCT/CN2018/075867, with translations.
Lihua E. Budde et al., Combining a CD20 Chimeric Antigen Receptor and an Inducible Caspase 9 Suicide Switch to Improve the Efficacy and Safety of T Cell Adoptive Immunotherapy for Lymphoma, PLOS One, vol. 8, No. 12, 2013, pp. 1-10.
Ku Matthew et al., Tumour cell surface antigen targeted therapies in B-cell lymphomas: Beyond rituximab, Blood Reviews, vol. 31, No. 1, 2016, pp. 23-35.
Andrew D. Fesnak et al., Engineered T Cells: The Promise and Challenges of Cancer Immunotherapy, Nature Reviews Cancer, vol. 16, No. 9, 2016, pp. 566-581 (in 2 parts).
Extended European Search Report in EP18751050.8, dated Oct. 15, 2020.
Jonnalagadda et al "ChimericAntigen Receptors With Mutated IgG4 Fc Spacer Avoid Fe Receptor Binding and Improve T Cell Persistence and Antitumor Efficacy." Molecular Therapy 2015; vol. 23 No. 4, 757-768.
Belovezhec T. N. Design and Comparative Analysis of CD20-Specific Chimeric Antigen Receptors. Proceedings of XIV International Conference of Students, Graduate Students and Young Scientists "Perspectives in Fundamental Sciences" Apr. 25-28, 2017. vol. 4: Biology and Basic Medical Sciences p. 22-24 (with translation).
Lopez-Atalaya et al. Development and Maintenance of the Brain's Immune Toolkit: Microglia and Non-Parenchymal Brain Macrophages. Dev Neurobiol. 2018; 78(6):561-579.
Riaz et al. Anti-CD19 and anti-CD20 CAR-modified T cells for B-cell malignancies: a systematic review and meta-analysis. Immunotherapy (2017) 9(12), 979-993.
Nakagawa et al. *Staphylococcus aureus* Virulent PSMa Peptides Induce Keratinocyte Alarmin Release to Orchestrate IL-17-Dependent Skin Inflammation. Cell Host & Microbe 2017; 22, 667-677.
Ramos et al. CAR-T Cell Therapy for Lymphoma. Annu. Rev. Med. 2016; 67: 165-183.
Shetty et al. Liver sinusoidal endothelial cells—gatekeepers of hepatic immunity. Nat Rev Gastroenterol Hepatol. 2018; 15(9): 555-567.
NCBI Accession AMZ04820, 2016, 1 page.
NCBI Accession ANS59202, 2016, 1 page.
Teeling et al. The Biological Activity of Human CD20 Monoclonal Antibodies Is Linked to Unique Epitopes on CD20. J Immunol 2006; 177: 362-371.
Korycka-Wolowiec et al. Ofatumumabfor treating chronic lymphocytic leukemia: a safety profile. Expert Opinion on Drug Safety 2015; 14(12): 1945-1959.
Jabbour et al. Monoclonal antibodies in acute lymphoblastic leukemia. Blood 2015; 125(26): 4010-4016.
Chuda et al. Ofatumumab: A Novel Anti-CD20Monoclonal Antibody for the Treatment of Chronic Lymphocytic Leukemia. Current Drug Therapy, 2012, 7, 281-289.
Teeling et al. (2004) Characterization of new human CD20 monoclonal antibodies with potent cytolytic activity against non-Hodgkin lymphomas. Blood 104: 1793-1800.
Lin TS (2010) Ofatumumab: a novel monoclonal ant CD20antibody. Pharmacogenomics and Personalized Medicine 3: 51-59.
Casan et al. (2018) Anti-CD20 monoclonal antibodies: reviewing a revolution. Human Vaccines & Immunotherapeutics 14(12): 2820-2841.
Till et al. (2012) CD20-specific adoptive immunotherapy for lymphoma using a chimeric antigen receptor with both CD28 and 4-1 BB domains: pilot clinical trial results. Blood 119(17): 3940-3950.
Hamdy et al. (2005) Sheep red blood cells armed with anti-CD20 single-chain variable fragments (scFvs) fused to a glycosylphosphatidylinositol (GPI) anchor: a strategy to target CD20-positive tumor cells. J. Immunol. Methods 297 (1-2): 109-124.
Gen Bank Accession AA022134.1 (2005), 2 pages.
Wu et al. (2001) Multimerization of a chimeric anti-CD20single-chain Fv-Fc fusion protein is mediated through variable domain exchange. Protein Eng. 14: 1025-1033.
Lulla et al. (2018) The Use of Chimeric Antigen Receptor T Cells in Patients with Non-Hodgkin Lymphoma Clinical Advances in Hematology & Oncology, 16(5): 375-386.
Hallek M. (2017) Chronic lymphocytic leukemia: 2017 update on diagnosis, risk stratification, and treatment. Am J Hematol. 92: 946-965.
Cao et al. (2019) Efficiency and safety of autologous chimeric antigen receptor T-cells therapy used for patients with lymphoma. Medicine 98: 42(e17506), 8 pages.
Till et al. (2008) Adoptive immunotherapy for indolent non-Hodgkin lymphoma and mantle cell lymphoma using genetically modified autologous CD20-spetific T cells. Blood112(6): 2261-2271.
Wang et al. (2014) Effective response and delayed toxicities of refractory advanced diffuse large B-cell lymphoma treated by CD20-directed chimeric antigen receptor-modified T cells. Clinical Immunology 155: 160-175.
Zhang et al. (2016) Treatment of CD20-directed Chimeric Antigen Receptor-modified T cells in patients with relapsed or refractory B-cell non-Hodgkin lymphoma: an early phase IIa trial report. Signal Transduction and Targeted Therapy 1: 16002; p. 1-10.
Jensen et al. (1998) CD20 is a molecular target for scFvFc:zeta receptor redirected T-cells: implications for cellular immunotherapy of CD20 malignancy. Biology of Blood and Marrow Transplant 4: 75-83.
Chow et al. (2019) Outcomes of patients with large B-cell lymphomas and progressive disease following CD19-specific CART-cell therapy. Am. J. Hematol. 94(8): E209-E213.
Patel, et al. (2020 "Expanding the Role of CAR-T Cell Therapy to Systemic Lupus Erythematosus" EMJ Hematology, 8(1): 105-12. (Year: 2020).
Non-final Office Action in U.S. Appl. No. 17/723,859, dated Aug. 4, 2022.
Non-final Office Action in U.S. Appl. No. 17/750,855, dated Aug. 5, 2022.
ClinicalTrials.gov, NCT03019055, Study of CAR-20/19-T Cells in Patients With Relapsed Refractory B Cell. 15 pages, Jul. 27, 2023.
Li et al., Clinical Responses and Pharmacokinetics of fully human BCMA Targeting CAR T Cell Therapy in Relapsed/Refractory Multiple Myeloma. 17th International Myeloma Workshop. pp. e23-e24, Abstract 0AB-033, Sep. 12-15, 2019.
Raje et al., Anti-BCMA CAR T-Cell Therapy bb2121 in Relapsed or Refractory Multiple Myeloma. N Engl J Med. May 2, 2019;380(18):1726-1737.
U.S. Appl. No. 17/475,766, filed Sep. 15, 2021, U.S. Pat. No. 11,439,665, Issued.
U.S. Appl. No. 17/721,647, filed Apr. 15, 2022, 2022-0249568, Published.
U.S. Appl. No. 17/750,658, filed May 23, 2022, U.S. Pat. No. 11,633,430, Issued.
U.S. Appl. No. 17/911,502, filed Sep. 14, 2022, 2023-0104705, Published.
U.S. Appl. No. 17/911,524, filed Sep. 14, 2022, 2023-0212255, Published.
U.S. Appl. No. 18/183,681, filed Mar. 14, 2023, 2024-0139243, Published.
U.S. Appl. No. 16/877,069, filed May 18, 2020, U.S. Pat. No. 11,207,349, Issued.
U.S. Appl. No. 16/484,482, filed Aug. 8, 2019, U.S. Pat. No. 11,066,457, Issued.

(56) References Cited

OTHER PUBLICATIONS

U.S. Appl. No. 17/352,915, filed Jun. 21, 2021, U.S. Pat. No. 11,472,858, Issued.
U.S. Appl. No. 17/723,859, filed Apr. 19, 2022, U.S. Pat. No. 11,618,778, Issued.
U.S. Appl. No. 17/750,855, filed May 23, 2022, U.S. Pat. No. 11,608,369, Issued.
U.S. Appl. No. 17/831,637, filed Jun. 3, 2022, 2022-0340640, Published.
U.S. Appl. No. 18/263,050, filed Jul. 26, 2023, 2024-0115605, Published.
International Search Report and Written Opinion of PCT/US22/13875, mailed Jul. 8, 2022.
Guedan et al., Engineering and Design of Chimeric Antigen Receptors. Mol Ther Methods Clin Dev. Mar. 15, 2019; 12:145-156.
Jayaraman et al., CAR-T design: Elements and their synergistic function. EBioMedicine. Aug. 2020;58: 102931, 12 pages.

* cited by examiner

CONSTRUCTION OF CHIMERIC ANTIGEN RECEPTOR TARGETING CD20 ANTIGEN AND ACTIVITY IDENTIFICATION OF ENGINEERED T CELLS THEREOF

CROSS-REFERENCE TO RELATED APPLICATIONS

This application is a continuation application of U.S. patent application Ser. No. 17/723,859, which is a continuation application of U.S. patent application Ser. No. 17/352,915, filed on Jun. 21, 2021, now U.S. Pat. No. 11,472,858, which is a continuation application of U.S. patent application Ser. No. 16/484,482, filed on Aug. 8, 2019, now U.S. Pat. No. 11,066,457, which is a 371 national stage of international application No. PCT/CN2018/075867, filed on Feb. 8, 2018, which claims priority to Chinese Patent Application No. CN201710069569.7, filed on Feb. 8, 2017, each of which is incorporated herein by reference in its entirety.

SEQUENCE LISTING

The instant application contains a Sequence Listing which has been submitted electronically in ST.26 XML format and is hereby incorporated by reference in its entirety. Said XML copy, created on Feb. 20, 2023, is named 11299-008883-US7_SL and is 70,102 bytes in size.

TECHNICAL FIELD

The present invention provides a sequence component of chimeric antigen receptor targeting CD20 antigen, and a preparation method for its modified T cells (CART20) and activity identification thereof. The present invention identifies a chimeric antigen receptor structure for treating CD20 positive B cell lymphoma.

BACKGROUND TECHNIQUE

Malignant tumors of the blood system account for about 10% of human malignant tumors, and 95% of malignant tumors of the blood system are derived from B lymphocytes. Traditional chemotherapy and radiotherapy play an important role in the treatment of malignant tumors of the blood system. Some patients also have significant effects, but most of them are difficult to cure. New and effective treatments have been a hot topic in this field.

Adoptive T cell therapy has shown its powerful efficacy and bright prospect in the clinical treatment of malignant tumors. Among them, multiple centers independently using Chimeric Antigen Receptor (CAR)-modified T cells to target recurrent, refractory malignant tumors of CD19-expressed B cell have achieved unprecedented success. In particular, in a clinical trial carried out at the School of Medicine, University of Pennsylvania using CART19 in the treatment of recurrent, refractory acute B-cell lymphoma (R/R B-ALL), up to 94% of patients achieved complete remission. Although the initial response rate of this clinical trial was high, nearly 40% of patients who achieved complete response after 1 month of treatment, had a relapse, and more than 60% of patients with relapse had CD19-negative tumor cells escape. Therefore, there is an urgent need to screen out CART structure that target B cell lymphoma-associated antigens other than CD19 to treat patients with malignant lymphoma.

CD20 is a glycosylated protein and is the first identified B cell membrane marker. CD20 is also known as B 1, and encoded by the MS4A gene. CD20 molecule has four transmembrane hydrophobic regions, and its N-terminal and C-terminal are located on the cytoplasmic side, thereby forming two closed loops outside the cell, which are respectively called big loop and small loop. CD20 is specifically expressed in more than 95% of normal and cancerous B cells. These cells are in the pre-B cell stage and subsequent developmental stages, and CD20 stops expression until the cells differentiated into plasma cells. Therefore, CD20 is an ideal target for immunotherapy of B cell malignancies.

Rituximab (MabThera®, Rituxan®) is the first generation of chimeric monoclonal antibody targeting CD20 which is firstly approved by the US FDA and the European EMA for treating indolent lymphoma. Rituximab recognizes and binds to the big loop structure of the extracellular domain of CD20, and it kills tumor cells by ADCC-mediated killing effect. However, Rituximab alone shows limited activity and short duration of response, but its combination with chemotherapy can significantly enhance the efficacy of chemotherapy. Rituximab is used for the treatment of lymphoma, and half of the patients have a complete response (CR) or a partial response (PR).

Ofatumumab (Arzerra®) is the first completely humanized CD20 therapeutic antibody. Unlike Rituximab, the epitope recognized by Ofatumumab contains parts of the big loop and the small loop of CD20. At the same time, the tumor killing method of Ofatumumab is mainly through the complement-dependent pathway, followed by ADCC-dependent tumor killing effect.

Obinutuzumab (Gazyvaro®, Gazyva®) is a humanized type II CD20 antibody that reduces fucosylation levels and optimizes FcγRIIIa affinity. Obinutuzumab recognizes and binds to the big loop of the extracellular molecule of CD20, and mediates the killing effect on tumor mainly through the ADCC effect. At the same time, the binding of Obinutuzumab to CD20 molecule also has the effect of inducing apoptosis of tumor cells. As for the NHL that does not respond to Rituximab treatment, Obinutuzumab is combined with bendamustine, a nitrogen mustard drug. The phase III clinical trial found that the duration with no deterioration of combination therapy of Obinutuzumab and bendamustine was twice as long as that of bendamustine therapy alone (the former is 29 months and the latter is 14 months). Obinutuzumab has an overall response rate (ORR, including CR and PR) of 77.3%, and Rituximab is 65.7%.

Compared with therapeutic antibodies, cellular immunotherapy is an emerging and highly effective tumor treatment model, and is a new type of autoimmunolgy treatment for cancer. It is a method for in vitro culture and amplification of immune cells collected from a patient using biotechnology and biological agents, and then the cells are transfused back to the patient to stimulate and enhance the body's autoimmune function, thereby achieving the purpose of treating tumors. The skilled in the art have been working to develop new cellular immunotherapy to increase its efficiency and reduce its side effect. Although many therapeutic antibodies as described above have been developed in these years, their clinical therapeutic effects have not reached the same level of therapeutic effects as CART19. Therefore, the development of CART therapy targeting CD20 has great market value and social significance.

SUMMARY OF THE INVENTION

In view of the differences in affinity and killing mechanisms of the therapeutic antibodies targeting CD20, we constructed a series of chimeric antigen receptors targeting CD20 using the DNA sequences of the antigen-binding regions of different antibodies, and completed the identification of anti-tumor activity and differential comparison of these chimeric antigen receptor engineering T cells in vitro. The invention provides new and effective methods and preparations for clinical application of CAR-T in the treatment of CD20-positive leukemia and lymphoma.

It is an object of the present invention to provide a chimeric antigen receptor targeting CD20, a preparation method and application thereof.

The present invention relates to the construction of a chimeric antigen receptor structure targeting CD20, a preparation method of a chimeric antigen receptor engineered T cell targeting CD20, and activity identification thereof.

In a first aspect of the invention, it provides a chimeric antigen receptor (CAR) (sequence), whose antigen binding domain (i.e., scFv) comprises an antibody heavy chain variable region as shown in SEQ ID NOs: 7 or 9 or 33 and an antibody light chain variable region as shown in SEQ ID NOs: 11 or 13 or 35.

In another preferred embodiment, the antigen binding domain of the chimeric antigen receptor is as follows:

$V_H$-$V_L$ wherein $V_H$ is an antibody heavy chain variable region; $V_L$ is an antibody light chain variable region; and "-" is a linker peptide or a peptide bond.

In another preferred embodiment, the amino acid sequence of the linker peptide is as shown in SEQ ID NO: 15.

In another preferred embodiment, the amino acid sequence of $V_H$ is as shown in SEQ ID NO: 7, and the amino acid sequence of $V_L$ is as shown in SEQ ID NO: 11.

In another preferred embodiment, the amino acid sequence of $V_H$ is as shown in SEQ ID NO: 9, and the amino acid sequence of $V_L$ is as shown in SEQ ID NO: 13.

In another preferred embodiment, the amino acid sequence of $V_H$ is as shown in SEQ ID NO: 33, and the amino acid sequence of $V_L$ is shown in SEQ ID NO: 35.

In another preferred embodiment, the structure of the chimeric antigen receptor is as follows:

L-$V_H$-$V_L$-H-TM-CS-CD3ζ wherein,

L is an optional leader sequence (i.e., signal peptide sequence);

H is a hinge region;

TM is a transmembrane domain;

CS is a co-stimulatory molecule derived from 4-1BB and/or CD28;

CD3ζ is a cytoplasmic signaling sequence derived from CD3ζ;

$V_H$, $V_L$, and "-" are as described above, respectively.

In another preferred embodiment, the sequence of L is as shown in SEQ ID NO: 27.

In another preferred embodiment, the sequence of H is as shown in SEQ ID NO: 17 or 19.

In another preferred embodiment, the sequence of TM comprises a transmembrane region derived from CD8a or CD28, preferably the sequence of TM is as shown in SEQ ID NO: 21 or 37.

In another preferred embodiment, the CS structure is: CD28-4-1BB, wherein CD28 is a co-stimulatory molecule derived from CD28; and 4-1BB is a co-stimulatory molecule derived from 4-1BB.

In another preferred embodiment, the sequence of the co-stimulatory molecule derived from 4-1BB is as shown in SEQ ID NO: 23.

In another preferred embodiment, the sequence of the co-stimulatory molecule derived from CD28 is as shown in SEQ ID NO: 39.

In another preferred embodiment, the sequence of CD3ζ is as shown in SEQ ID NO: 25.

In another preferred embodiment, the sequence of the chimeric antigen receptor is as shown in SEQ ID NOs: 1, 3, 5, 29, or 31.

In a second aspect of the invention, a nucleic acid molecule is provided, encoding the chimeric antigen receptor (CAR) of the first aspect of the invention.

In another preferred embodiment, the nucleic acid molecule comprises a nucleic acid sequence encoding the hinge region selected from the group consisting of:

(a) a polynucleotide encoding a polypeptide as shown in SEQ ID NO: 17 or 19;

(b) a polynucleotide having a sequence as shown in SEQ ID NO: 18 or 20;

(c) a polynucleotide having a nucleotide sequence with ≥90% (preferably ≥95%) homologous to the sequence of SEQ ID NO: 18 or 20, and encoding the amino acid sequence of SEQ ID NO: 17 or 19;

(d) a polynucleotide complementary to the polynucleotide of any of (a) to (c).

In another preferred embodiment, the nucleic acid molecule comprises a nucleic acid sequence encoding the CD8a transmembrane region selected from the group consisting of:

(a) a polynucleotide encoding a polypeptide as shown in SEQ ID NO: 21;

(b) a polynucleotide having a sequence as shown in SEQ ID NO: 22;

(c) a polynucleotide having a nucleotide sequence with ≥90% (preferably ≥95%) homologous to the sequence of SEQ ID NO: 22 and encoding the amino acid sequence of SEQ ID NO: 21;

(d) a polynucleotide complementary to the polynucleotide of any of (a) to (c).

In another preferred embodiment, the nucleic acid molecule comprises a nucleic acid sequence encoding the 4-1BB (CD137) intracellular signal domain selected from the group consisting of:

(a) a polynucleotide encoding a polypeptide as shown in SEQ ID NO: 23;

(b) a polynucleotide having a sequence as shown in SEQ ID NO: 24;

(c) a polynucleotide having a nucleotide sequence with ≥90% (preferably ≥95%) homologous to the sequence of SEQ ID NO: 24 and encoding the amino acid sequence of SEQ ID NO: 23;

(d) a polynucleotide complementary to the polynucleotide of any of (a) to (c).

In another preferred embodiment, the nucleic acid molecule comprises a nucleic acid sequence encoding the CD28 intracellular signal domain selected from the group consisting of:

(a) a polynucleotide encoding a polypeptide as shown in SEQ ID NO: 39;

(b) a polynucleotide having a sequence as shown in SEQ ID NO: 40;

(c) a polynucleotide having a nucleotide sequence with ≥90% (preferably ≥95%) homologous to the sequence of SEQ ID NO: 40 and encoding the amino acid sequence of SEQ ID NO: 39;

(d) a polynucleotide complementary to the polynucleotide of any of (a) to (c).

In another preferred embodiment, the nucleic acid molecule comprises a nucleic acid sequence encoding the CD3ζ intracellular signal domain selected from the group consisting of:

(a) a polynucleotide encoding a polypeptide as shown in SEQ ID NO: 25;

(b) a polynucleotide having a sequence as shown in SEQ ID NO: 26;

(c) a polynucleotide having a nucleotide sequence with ≥90% (preferably ≥95%) homologous to the sequence of SEQ ID NO: 26 and encoding the amino acid sequence of SEQ ID NO: 25;

(d) a polynucleotide complementary to the polynucleotide of any of (a) to (c).

In another preferred embodiment, the nucleic acid molecule comprises a nucleic acid sequence selected from the group consisting of:

(a) a polynucleotide encoding a polypeptide as shown in SEQ ID NOs: 1, 35, 29 or 31;

(b) a polynucleotide having the sequence as shown in SEQ ID NOs: 2, 4, 6, 30 or 32;

(c) a polynucleotide having a nucleotide sequence with ≥95% (preferably ≥98%) homologous to the sequence of SEQ ID NOs: 2, 4, 6, 30 or 32, and encoding the amino acid sequence of SEQ ID NOs: 1, 35, 29 or 31;

(d) a polynucleotide complementary to the polynucleotide of any of (a) to (c).

In another preferred embodiment, the nucleic acid molecule is isolated.

In another preferred embodiment, the nucleic acid molecule further comprises a polynucleotide encoding the leader sequence (directing sequence, signal peptide), and the amino acid sequence of the leader sequence is as shown in SEQ ID NO: 27; preferably the polynucleotide encoding the leader sequence (signal peptide) is as shown in SEQ ID NO: 28.

In another preferred embodiment, the sequence of the nucleic acid molecule is as shown in SEQ ID NOs: 2, 46, 30 or 32.

In a third aspect of the invention, it provides a vector, comprising the nucleic acid molecule of the second aspect of the invention.

In another preferred embodiment, the vector is a lentiviral vector.

In a fourth aspect of the invention, it provides a host cell comprising the vector of the third aspect of the invention or having the exogenous nucleic acid molecule of the second aspect of the invention integrated into its genome.

In another preferred embodiment, the cell is an isolated cell, and/or the cell is a genetically engineered cell.

In another preferred embodiment, the cell is a mammalian cell.

In another preferred embodiment, the cell is a T cell.

In a fifth aspect of the invention, it provides a pharmaceutical composition comprising a pharmaceutically acceptable carrier and the chimeric antigen receptor of the first aspect of the invention, the nucleic acid molecule of the second aspect of the invention, the vector of the third aspect of the invention, or the cell of the fourth aspect of the invention.

In a sixth aspect of the invention, it provides the use of the chimeric antigen receptor of the first aspect of the invention, the nucleic acid molecule of the second aspect of the invention, the vector of the third aspect of the invention, or the cell of the fourth aspect of the invention for the preparation of a medicine or a formulation for treating tumor or autoimmune disease.

In another preferred embodiment, the autoimmune disease is an autoimmune disease caused by overexpression of B cells (such as lupus erythematosus).

In another preferred embodiment, the tumor comprises CD20 positive tumor.

In a seventh aspect of the invention, it provides a method for treating a disease comprising administering an appropriate amount of the chimeric antigen receptor of the first aspect of the invention, the nucleic acid molecule of the second aspect of the invention, the vector of the third aspect of the invention, the cell of the fourth aspect of the invention, or the pharmaceutical composition of the fifth aspect of the invention, to a subject in need of treatment.

In another preferred embodiment, the disease is tumor.

In an eighth aspect of the invention, it provides a method for preparing a CAR-T cell (CAR-modified T cell) expressing the chimeric antigen receptor of the first aspect of the invention, comprising the steps of: transducing the nucleic acid molecule of the second aspect of the invention or the vector of the third aspect of the invention into a T cell, thereby obtaining the CAR-T cell.

It is to be understood that the various technical features of the present invention mentioned above and the various technical features specifically described hereinafter (as in the Examples) may be combined with each other within the scope of the present invention to constitute a new or preferred technical solution, which will not be repeated one by one herein.

MODES FOR CARRYING OUT THE PRESENT INVENTION

Figure 1:
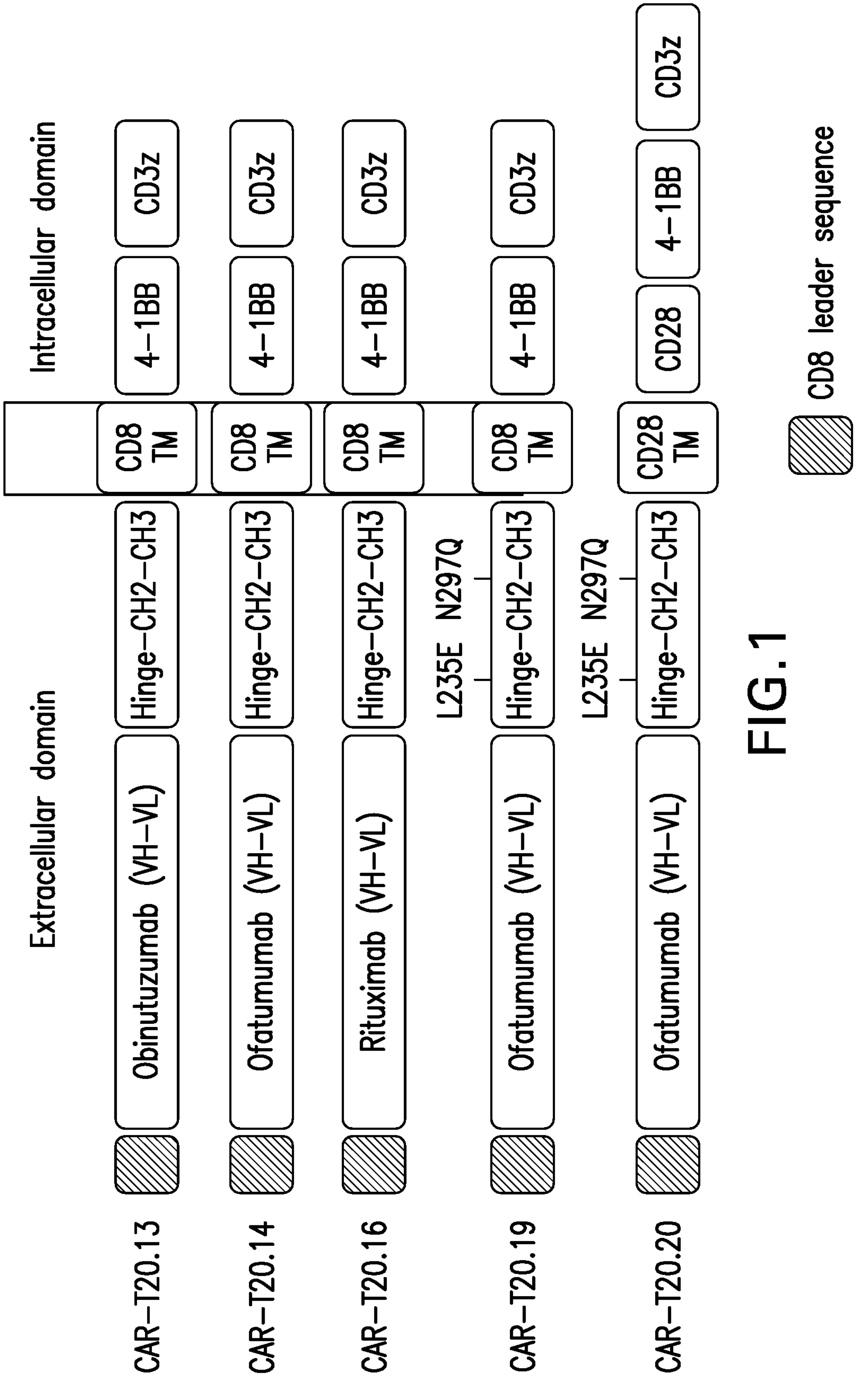
FIG. 1 shows the structure of the chimeric antigen receptor targeting CD20. Each element of the designed CAR structure is shown in the figure, and the listed elements include: a leader sequence, an antigen recognition sequence (Ofatumumaband, Obinutuzumab, Rituximab), a hinge region, a transmembrane region, a co-stimulatory factor signal region, and a CD3ζ signaling region. CAR-T20.14, CAR-T20.13 and CAR-T20.16 are CAR structures constructed based on the antibody variable region sequences of Ofatumumab, Obinutuzumab and Rituxmab, respectively. CAR-T20.19 and CAR-20.20 are the mutant form of CAR-T20.14, having L235E-N297Q mutation in IgG4 Hinge-CH2-CH3 linker region. CAR-T20.20 is a third generation chimeric antigen receptor structure with coding sequences of both CD28 and 4-1BB co-stimulatory signaling molecule.

After extensive and intensive studies, the inventors have obtained a chimeric antigen receptor targeting CD20 and the preparation and application thereof. The extracellular antigen binding domain of the chimeric antigen receptor includes the antibody heavy chain variable region shown in SEQ ID NO: 1 and the antibody light chain variable region shown in SEQ ID NO: 2. The experimental results show that the chimeric antigen receptor provided by the present invention shows extremely high killing ability against tumor cells.

In view of the differences in affinity, killing mechanism of therapeutic antibodies targeting CD20, as well as the significant effects of different transmembrane domains and intracellular domains on the activity of chimeric antigen receptor, a series of chimeric antigen receptors targeting CD20 were constructed in the present invention by combining various transmembrane and intracellular components with the amino acid sequences of the variable regions in various anti-CD20 antibodies. The expression of such chimeric antigen receptors in primary T cells was completed. The detection method of receptor expression intensity was established. The ability of the CAR-T cells to recognize CD20 antigen in vitro and in vivo, as well as the difference in the activity of scavenging malignant tumors carrying CD20 antigen in vitro and in vivo were identified, providing a new effective method and preparation for the clinical application of CAR T in treating CD20 positive leukemia and lymphoma.

Chimeric Antigen Receptor

The invention provides a chimeric antigen receptor (CAR) comprising an extracellular domain, a transmembrane domain, and an intracellular domain. The extracellular domain comprises a target-specific binding element (also known as an antigen binding domain). The intracellular domain includes a co-stimulatory signaling region and a chain moiety. The co-stimulatory signaling region refers to a part of the intracellular domain that includes a co-stimulatory molecule. The co-stimulatory molecule is a cell surface molecule required for efficient response of lymphocytes to antigens, rather than an antigen receptor or its ligand.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that plays a role of linking the transmembrane domain to the extracellular domain or the cytoplasmic domain in a polypeptide chain. The linker may comprise 0-300 amino acids, preferably 2-100 amino acids and most preferably 3-50 amino acids.

In a preferred embodiment of the invention, the extracellular domain of the CAR provided by the invention comprises an antigen binding domain targeting CD20. When the CAR of the present invention is expressed in T cell, antigen recognition can be performed based on antigen binding specificity. When it binds to its cognate antigen, it affects a tumor cell so that the tumor cell fails to grow, is prompted to die, or otherwise is affected so that the tumor burden in a patient is diminished or eliminated. The antigen binding domain is preferably fused with an intracellular domain from one or more of a co-stimulatory molecule and a chain. Preferably, the antigen binding domain is fused with an intracellular domain of a combination of a 4-1BB signaling domain and/or a CD28 signaling domain, and a CD3ζ signaling domain.

In one embodiment, the CAR targeting CD20 of the invention comprises the specific signaling domain of the invention (the transmembrane region of CD8, the intracellular signal domains of CD137 and CD3ζ are made in series). The signaling domain of the invention significantly increases anti-tumor activity and in vivo persistence of CAR-T cells compared to an otherwise identical CAR targeting CD20.

In a preferred embodiment of the invention, the amino acid sequence of the chimeric antigen receptor (CAR) provided by the present invention is as follows:

```
CAR-T20.13
                                                         (SEQ ID NO: 29)
MALPVTALLL PLALLLHAAR PQVQLVQSGA EVKKPGSSVK VSCKASGYAF SYSWINWVRQ    60

APGQGLEWMG RIFPGDGDTD YNGKFKGRVT ITADKSTSTA YMELSSLRSE DTAVYYCARN   120

VFDGYWLVYW GQGTLVTVSS GGGGSGGGGS GGGGSDIVMT QTPLSLPVTP GEPASISCRS   180

SKSLLHSNGI TYLYWYLQKP GQSPQLLIYQ MSNLVSGVPD RFSGSGSGTD FTLKISRVEA   240
```

-continued

```
EDVGVYYCAQ NLELPYTFGG GTKVEIKRTV ESKYGPPCPP CPAPEFLGGP SVFLFPPKPK    300

DTLMISRTPE VTCVVVDVSQ EDPEVQFNWY VDGVEVHNAK TKPREEQFNS TYRVVSVLTV    360

LHQDWLNGKE YKCKVSNKGL PSSIEKTISK AKGQPREPQV YTLPPSQEEM TKNQVSLTCL    420

VKGFYPSDIA VEWESNGQPE NNYKTTPPVL DSDGSFFLYS RLTVDKSRWQ EGNVFSCSVM    480

HEALHNHYTQ KSLSLSLGKI YIWAPLAGTC GVLLLSLVIT LYCKRGRKKL LYIFKQPFMR    540

PVQTTQEEDG CSCRFPEEEE GGCELRVKFS RSADAPAYKQ GQNQLYNELN LGRREEYDVL    600

DKRRGRDPEM GGKPRRKNPQ EGLYNELQKD KMAEAYSEIG MKGERRRGKG HDGLYQGLST    660

ATKDTYDALH MQALPPR                                                   677
```

The DNA sequence encoding CAR-T20.13 (SEQ ID NO: 30) is as follows:

```
atggccttac cagtgaccgc cttgctcctg ccgctggcct tgctgctcca cgccgccagg   60

ccgcaggtgc aattggtgca gtctggcgct gaagttaaga agcctgggag ttcagtgaag  120

gtctcctgca aggcttccgg atacgccttc agctattctt ggatcaattg ggtgcggcag  180

gcgcctggac aagggctcga gtggatggga cggatctttc ccggcgatgg ggatactgac  240

tacaatggga aattcaaggg cagagtcaca attaccgccg acaaatccac tagcacagcc  300

tatatggagc tgagcagcct gagatctgag gacacggccg tgtattactg tgcaagaaat  360

gtctttgatg gttactggct tgtttactgg ggccagggaa ccctggtcac cgtctcctca  420

ggtggcggtg gctcgggcgg tggtgggtcg ggtggcggcg gatctgatat cgtgatgacc  480

cagactccac tctccctgcc cgtcacccct ggagagcccg ccagcattag ctgcaggtct  540

agcaagagcc tcttgcacag caatggcatc acttatttgt attggtacct gcaaaagcca  600

gggcagtctc cacagctcct gatttatcaa atgtccaacc ttgtctctgg cgtccctgac  660

cggttctccg gctccgggtc aggcactgat ttcacactga aaatcagcag ggtggaggct  720

gaggatgttg gagtttatta ctgcgctcag aatctagaac ttccttacac cttcggcgga  780

gggaccaagg tggagatcaa acgtacggtg gagagcaagt acggaccgcc ctgccccct  840

tgccctgccc ccgagttcct gggcggaccc agcgtgttcc tgttcccccc caagcccaag  900

gacaccctga tgatcagccg gacccccgag gtgacctgcg tggtggtgga cgtgagccag  960

gaagatcccg aggtccagtt caattggtac gtggacggcg tggaagtgca caacgccaag 1020

accaagccca gagaggaaca gttcaacagc acctaccggg tggtgtctgt gctgaccgtg 1080

ctgcaccagg actggctgaa cggcaaagaa tacaagtgca aggtgtccaa caagggcctg 1140

cccagcagca tcgaaaagac catcagcaag gccaagggcc agcctcgcga gccccaggtg 1200

tacaccctgc ctccctccca ggaagagatg accaagaacc aggtgtccct gacctgcctg 1260

gtgaagggct tctaccccag cgacatcgcc gtggagtggg agagcaacgg ccagcctgag 1320

aacaactaca agaccacccc tcccgtgctg gacagcgacg gcagcttctt cctgtacagc 1380

cggctgaccg tggacaagag ccggtggcag gaaggcaacg tctttagctg cagcgtgatg 1440

cacgaggccc tgcacaacca ctacacccag aagagcctga gcctgtccct gggcaagatc 1500

tacatctggg cgcccttggc cgggacttgt ggggtccttc tcctgtcact ggttatcacc 1560

ctttactgca aacggggcag aaagaaactc ctgtatatat tcaaacaacc atttatgaga 1620

ccagtacaaa ctactcaaga ggaagatggc tgtagctgcc gatttccaga agaagaagaa 1680

ggaggatgtg aactgagagt gaagttcagc aggagcgcag acgcccccgc gtacaagcag 1740

ggccagaacc agctctataa cgagctcaat ctaggacgaa gagaggagta cgatgttttg 1800
```

-continued

```
gacaagagac gtggccggga ccctgagatg gggggaaagc cgagaaggaa gaaccctcag 1860
gaaggcctgt acaatgaact gcagaaagat aagatggcgg aggcctacag tgagattggg 1920
atgaaaggcg agcgccggag gggcaagggg cacgatggcc tttaccaggg tctcagtaca 1980
gccaccaagg acacctacga cgcccttcac atgcaggccc tgccccctcg ctag       2034
```

CAR-T20.14(SEQ ID NO: 1):

```
MALPVTALLL PLALLLHAAR PEVQLVESGG GLVQPGRSLR LSCAASGFTF NDYAMHWVRQ   60
APGKGLEWVS TISWNSGSIG YADSVKGRFT ISRDNAKKSL YLQMNSLRAE DTALYYCAKD  120
IQYGNYYYGM DVWGQGTTVT VSSGGGGSGG GGSGGGGSEI VLTQSPATLS LSPGERATLS  180
CRASQSVSSY LAWYQQKPGQ APRLLIYDAS NRATGIPARF SGSGSGTDFT LTISSLEPED  240
FAVYYCQQRS NWPITFGQGT RLEIKESKYG PPCPPCPAPE FLGGPSVFLF PPKPKDTLMI  300
SRTPEVTCVV VDVSQEDPEV QFNWYVDGVE VHNAKTKPRE EQFNSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKIYIWAP LAGTCGVLLL SLVITLYCKR GRKKLLYIFK QPFMRPVQTT  540
QEEDGCSCRF PEEEEGGCEL RVKFSRSADA PAYKQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                      672
```

The DNA sequence encoding CAR-T20.14 (SEQ ID NO: 2) is as follows:

```
atggccttac cagtgaccgc cttgctcctg ccgctggcct tgctgctcca cgccgccagg     60
ccggaagtgc agctggtgga gtctgggggga ggcttggtac agcctggcag gtccctgaga    120
ctctcctgtg cagcctctgg attcaccttt aatgattatg ccatgcactg ggtccggcaa    180
gctccaggga agggcctgga gtgggtctca actattagtt ggaatagtgg ttccataggc    240
tatgcggact ctgtgaaggg ccgattcacc atctccagag acaacgccaa gaagtccctg    300
tatctgcaaa tgaacagtct gagagctgag gacacggcct tgtattactg tgcaaaagat    360
atacagtacg gcaactacta ctacggtatg gacgtctggg gccaagggac cacggtcacc    420
gtctcctcag gtggcggtgg ctcgggcggt ggtgggtcgg gtggcggcgg atctgaaatt    480
gtgttgacac agtctccagc caccctgtct ttgtctccag gggaaagagc caccctctcc    540
tgcagggcca gtcagagtgt tagcagctac ttagcctggt accaacagaa acctggccag    600
gctcccaggc tcctcatcta tgatgcatcc aacagggcca ctggcatccc agccaggttc    660
agtggcagtg ggtctgggac agacttcact ctcaccatca gcagcctaga gcctgaagat    720
tttgcagttt attactgtca gcagcgtagc aactggccga tcaccttcgg ccaagggaca    780
cgactggaga ttaaagagag caagtacgga ccgccctgcc ccccttgccc tgccccccgag    840
ttcctgggcg gacccagcgt gttcctgttc ccccccaagc ccaaggacac cctgatgatc    900
agccggaccc ccgaggtgac ctgcgtggtg gtggacgtga gccaggaaga tcccgaggtc    960
cagttcaatt ggtacgtgga cggcgtggaa gtgcacaacg ccaagaccaa gcccagagag   1020
gaacagttca acagcaccta ccgggtggtg tctgtgctga ccgtgctgca ccaggactgg   1080
ctgaacggca aagaatacaa gtgcaaggtg tccaacaagg gcctgcccag cagcatcgaa   1140
aagaccatca gcaaggccaa gggccagcct cgcgagcccc aggtgtacac cctgcctccc   1200
```

-continued

```
tcccaggaag agatgaccaa gaaccaggtg tccctgacct gcctggtgaa gggcttctac     1260

cccagcgaca tcgccgtgga gtgggagagc aacggccagc ctgagaacaa ctacaagacc     1320

acccctcccg tgctggacag cgacggcagc ttcttcctgt acagccggct gaccgtggac     1380

aagagccggt ggcaggaagg caacgtcttt agctgcagcg tgatgcacga ggccctgcac     1440

aaccactaca cccagaagag cctgagcctg tccctgggca agatctacat ctgggcgccc     1500

ttggccggga cttgtggggt ccttctcctg tcactggtta tcacccttta ctgcaaacgg     1560

ggcagaaaga aactcctgta tatattcaaa caaccattta tgagaccagt acaaactact     1620

caagaggaag atggctgtag ctgccgattt ccagaagaag aagaaggagg atgtgaactg     1680

agagtgaagt tcagcaggag cgcagacgcc cccgcgtaca agcagggcca gaaccagctc     1740

tataacgagc tcaatctagg acgaagagag gagtacgatg ttttggacaa gagacgtggc     1800

cgggaccctg agatgggggg aaagccgaga aggaagaacc ctcaggaagg cctgtacaat     1860

gaactgcaga aagataagat ggcggaggcc tacagtgaga ttgggatgaa aggcgagcgc     1920

cggaggggca aggggcacga tggcctttac cagggtctca gtacagccac caaggacacc     1980

tacgacgccc ttcacatgca ggccctgccc cctcgctag                            2019
```

CAR-T20.16

```
                                                          (SEQ ID NO: 3)
MALPVTALLL PLALLLHAAR PQVQLQQPGA ELVKPGASVK MSCKASGYTF TSYNMHWVKQ      60

TPGRGLEWIG AIYPGNGDTS YNQKFKGKAT LTADKSSSTA YMQLSSLTSE DSAVYYCARS     120

TYYGGDWYFN VWGAGTTVTV SAGGGGSGGG GSGGGGSQIV LSQSPAILSA SPGEKVTMTC     180

RASSSVSYIH WFQQKPGSSP KPWIYATSNL ASGVPVRFSG SGSGTSYSLT ISRVEAEDAA     240

TYYCQQWTSN PPTFGGGTKL EIKESKYGPP CPPCPAPEFL GGPSVFLFPP KPKDTLMISR     300

TPEVTCVVVD VSQEDPEVQF NWYVDGVEVH NAKTKPREEQ FNSTYRVVSV LTVLHQDWLN     360

GKEYKCKVSN KGLPSSIEKT ISKAKGQPRE PQVYTLPPSQ EEMTKNQVSL TCLVKGFYPS     420

DIAVEWESNG QPENNYKTTP PVLDSDGSFF LYSRLTVDKS RWQEGNVFSC SVMHEALHNH     480

YTQKSLSLSL GKIYIWAPLA GTCGVLLLSL VITLYCKRGR KKLLYIFKQP FMRPVQTTQE     540

EDGCSCRFPE EEEGGCELRV KFSRSADAPA YKQGQNQLYN ELNLGRREEY DVLDKRRGRD     600

PEMGGKPRRK NPQEGLYNEL QKDKMAEAYS EIGMKGERRR GKGHDGLYQG LSTATKDTYD     660

ALHMQALPPR                                                            670
```

The DNA sequence encoding CAR-T20.16 (SEQ ID NO: 4) is as follows:

```
ATGGCCTTAC CAGTGACCGC CTTGCTCCTG CCGCTGGCCT TGCTGCTCCA CGCCGCCAGG      60

CCGCAGGTGC AGTTGCAACA GCCTGGAGCT GAGTTGGTGA AGCCTGGTGC TTCTGTGAAG     120

ATGTCTTGTA AGGCTTCTGG ATACACATTC ACTTCTTACA ACATGCACTG GGTGAAGCAG     180

ACTCCTGGTA GGGGTTTGGA GTGGATCGGA GCTATCTACC CAGGAAACGG AGACACATCT     240

TACAACCAGA AGTTCAAGGG TAAGGCTACA TTGACTGCTG ACAAGTCTTC ATCTACTGCT     300

TACATGCAAT TGTCTTCTTT GACATCTGAG GACTCTGCAG TTTACTACTG CGCTAGGTCT     360

ACATACTACG GAGGTGACTG GTACTTCAAC GTGTGGGGAG CAGGTACCAC GGTCACTGTC     420

TCTGCAGGTG GAGGTGGATC TGGAGGAGGA GGATCTGGTG GAGGAGGTTC TCAAATTGTT     480

CTCTCCCAGT CTCCAGCAAT CCTGTCAGCT TCTCCTGGAG AGAAGGTGAC TATGACTTGC     540

AGGGCTTCTT CATCTGTTTC TTACATCCAC TGGTTCCAGC AGAAGCCTGG TTCTTCACCT     600

AAGCCTTGGA TCTACGCTAC ATCTAACTTG GCATCTGGAG TGCCTGTGAG GTTCTCTGGT     660
```

-continued

```
TCTGGTTCAG GTACTTCTTA CTCTTTGACA ATCTCTAGGG TGGAGGCTGA GGACGCTGCT     720

ACTTACTACT GCCAGCAGTG GACATCTAAC CCTCCAACAT TCGGAGGTGG TACTAAGTTG     780

GAGATCAAGG AGAGCAAGTA CGGACCGCCC TGCCCCCCTT GCCCTGCCCC CGAGTTCCTG     840

GGCGGACCCA GCGTGTTCCT GTTCCCCCCC AAGCCCAAGG ACACCCTGAT GATCAGCCGG     900

ACCCCCGAGG TGACCTGCGT GGTGGTGGAC GTGAGCCAGG AAGATCCCGA GGTCCAGTTC     960

AATTGGTACG TGGACGGCGT GGAAGTGCAC AACGCCAAGA CCAAGCCCAG AGAGGAACAG    1020

TTCAACAGCA CCTACCGGGT GGTGTCTGTG CTGACCGTGC TGCACCAGGA CTGGCTGAAC    1080

GGCAAAGAAT ACAAGTGCAA GGTGTCCAAC AAGGGCCTGC CCAGCAGCAT CGAAAAGACC    1140

ATCAGCAAGG CCAAGGGCCA GCCTCGCGAG CCCCAGGTGT ACACCCTGCC TCCCTCCCAG    1200

GAAGAGATGA CCAAGAACCA GGTGTCCCTG ACCTGCCTGG TGAAGGGCTT CTACCCCAGC    1260

GACATCGCCG TGGAGTGGGA GAGCAACGGC CAGCCTGAGA ACAACTACAA GACCACCCCT    1320

CCCGTGCTGG ACAGCGACGG CAGCTTCTTC CTGTACAGCC GGCTGACCGT GGACAAGAGC    1380

CGGTGGCAGG AAGGCAACGT CTTTAGCTGC AGCGTGATGC ACGAGGCCCT GCACAACCAC    1440

TACACCCAGA AGAGCCTGAG CCTGTCCCTG GGCAAGATCT ACATCTGGGC GCCCTTGGCC    1500

GGGACTTGTG GGGTCCTTCT CCTGTCACTG GTTATCACCC TTTACTGCAA ACGGGGCAGA    1560

AAGAAACTCC TGTATATATT CAAACAACCA TTTATGAGAC CAGTACAAAC TACTCAAGAG    1620

GAAGATGGCT GTAGCTGCCG ATTTCCAGAA GAAGAAGAAG GAGGATGTGA ACTGAGAGTG    1680

AAGTTCAGCA GGAGCGCAGA CGCCCCCGCG TACAAGCAGG GCCAGAACCA GCTCTATAAC    1740

GAGCTCAATC TAGGACGAAG AGAGGAGTAC GATGTTTTGG ACAAGAGACG TGGCCGGGAC    1800

CCTGAGATGG GGGGAAAGCC GAGAAGGAAG AACCCTCAGG AAGGCCTGTA CAATGAACTG    1860

CAGAAAGATA AGATGGCGGA GGCCTACAGT GAGATTGGGA TGAAAGGCGA GCGCCGGAGG    1920

GGCAAGGGGC ACGATGGCCT TTACCAGGGT CTCAGTACAG CCACCAAGGA CACCTACGAC    1980

GCCCTTCACA TGCAGGCCCT GCCCCCTCGC TAG                                2013
```

In another more preferred embodiment of the invention, the amino acid sequence of the chimeric antigen receptor (CAR) provided by the invention is as follows:

```
CAR-T20.19
                                                          (SEQ ID NO: 5)
MALPVTALLL PLALLLHAAR PEVQLVESGG GLVQPGRSLR LSCAASGFTF NDYAMHWVRQ      60

APGKGLEWVS TISWNSGSIG YADSVKGRFT ISRDNAKKSL YLQMNSLRAE DTALYYCAKD     120

IQYGNYYYGM DVWGQGTTVT VSSGGGGSGG GGSGGGGSEI VLTQSPATLS LSPGERATLS     180

CRASQSVSSY LAWYQQKPGQ APRLLIYDAS NRATGIPARF SGSGSGTDFT LTISSLEPED     240

FAVYYCQQRS NWPITFGQGT RLEIKESKYG PPCPPCPAPE FEGGPSVFLF PPKPKDTLMI     300

SRTPEVTCVV VDVSQEDPEV QFNWYVDGVE VHNAKTKPRE EQFQSTYRVV SVLTVLHQDW     360

LNGKEYKCKV SNKGLPSSIE KTISKAKGQP REPQVYTLPP SQEEMTKNQV SLTCLVKGFY     420

PSDIAVEWES NGQPENNYKT TPPVLDSDGS FFLYSRLTVD KSRWQEGNVF SCSVMHEALH     480

NHYTQKSLSL SLGKIYIWAP LAGTCGVLLL SLVITLYCKR GRKKLLYIFK QPFMRPVQTT     540

QEEDGCSCRF PEEEEGGCEL RVKFSRSADA PAYKQGQNQL YNELNLGRRE EYDVLDKRRG     600

RDPEMGGKPR RKNPQEGLYN ELQKDKMAEA YSEIGMKGER RRGKGHDGLY QGLSTATKDT     660

YDALHMQALP PR                                                         672
```

The DNA sequence encoding CAR-T20.19 (SEQ ID NO: 6) is as follows:

```
atggccttac cagtgaccgc cttgctcctg ccgctggcct tgctgctcca cgccgccagg      60

ccggaagtgc agctggtgga gtctggggga ggcttggtac agcctggcag gtccctgaga     120

ctctcctgtg cagcctctgg attcaccttt aatgattatg ccatgcactg ggtccggcaa     180

gctccaggga agggcctgga gtgggtctca actattagtt ggaatagtgg ttccataggc     240

tatgcggact ctgtgaaggg ccgattcacc atctccagag acaacgccaa gaagtccctg     300

tatctgcaaa tgaacagtct gagagctgag gacacggcct tgtattactg tgcaaaagat     360

atacagtacg gcaactacta ctacggtatg gacgtctggg gccaagggac cacggtcacc     420

gtctcctcag gtggcggtgg ctcgggcggt ggtgggtcgg gtggcggcgg atctgaaatt     480

gtgttgacac agtctccagc caccctgtct ttgtctccag gggaaagagc caccctctcc     540

tgcagggcca gtcagagtgt tagcagctac ttagcctggt accaacagaa acctggccag     600

gctcccaggc tcctcatcta tgatgcatcc aacagggcca ctggcatccc agccaggttc     660

agtggcagtg ggtctgggac agacttcact ctcaccatca gcagcctaga gcctgaagat     720

tttgcagttt attactgtca gcagcgtagc aactggccga tcaccttcgg ccaagggaca     780

cgactggaga ttaaagagag caagtacgga ccgccctgcc ccccttgccc tgcccccgag     840

ttcgagggcg gacccagcgt gttcctgttc ccccccaagc ccaaggacac cctgatgatc     900

agccggaccc ccgaggtgac ctgcgtggtg gtggacgtga gccaggaaga tcccgaggtc     960

cagttcaatt ggtacgtgga cggcgtggaa gtgcacaacg ccaagaccaa gcccagagag    1020

gaacagttcc aaagcaccta ccgggtggtg tctgtgctga ccgtgctgca ccaggactgg    1080

ctgaacggca aagaatacaa gtgcaaggtg tccaacaagg gcctgcccag cagcatcgaa    1140

aagaccatca gcaaggccaa gggccagcct cgcgagcccc aggtgtacac cctgcctccc    1200

tcccaggaag agatgaccaa gaaccaggtg tccctgacct gcctggtgaa gggcttctac    1260

cccagcgaca togccgtgga gtgggagagc aacggccagc ctgagaacaa ctacaagacc    1320

acccctcccg tgctggacag cgacggcagc ttcttcctgt acagccggct gaccgtggac    1380

aagagccggt ggcaggaagg caacgtcttt agctgcagcg tgatgcacga ggccctgcac    1440

aaccactaca cccagaagag cctgagcctg tccctgggca agatctacat ctgggcgccc    1500

ttggccggga cttgtggggt ccttctcctg tcactggtta tcacccttta ctgcaaacgg    1560

ggcagaaaga aactcctgta tatattcaaa caaccattta tgagaccagt acaaactact    1620

caagaggaag atggctgtag ctgccgattt ccagaagaag aagaaggagg atgtgaactg    1680

agagtgaagt tcagcaggag cgcagacgcc cccgcgtaca agcagggcca gaaccagctc    1740

tataacgagc tcaatctagg acgaagagag gagtacgatg ttttggacaa gagacgtggc    1800

cgggaccctg agatgggggg aaagccgaga aggaagaacc ctcaggaagg cctgtacaat    1860

gaactgcaga aagataagat ggcggaggcc tacagtgaga ttgggatgaa aggcgagcgc    1920

cggaggggca aggggcacga tggcctttac cagggtctca gtacagccac caaggacacc    1980

tacgacgccc ttcacatgca ggccctgccc cctcgctag                           2019
```

In another most preferred embodiment of the invention, the amino acid sequence of the chimeric antigen receptor (CAR) provided by the invention is as follows:

```
CAR-T20.20
                                                     (SEQ ID NO: 31)
MALPVTALLL PLALLLHAAR PEVQLVESGG GLVQPGRSLR LSCAASGFTF NDYAMHWVRQ   60

APGKGLEWVS TISWNSGSIG YADSVKGRFT ISRDNAKKSL YLQMNSLRAE DTALYYCAKD  120

IQYGNYYYGM DVWGQGTTVT VSSGGGGSGG GGSGGGGSEI VLTQSPATLS LSPGERATLS  180

CRASQSVSSY LAWYQQKPGQ APRLLIYDAS NRATGIPARF SGSGSGTDFT LTISSLEPED  240

FAVYYCQQRS NWPITFGQGT RLEIKESKYG PPCPPCPAPE FEGGPSVFLF PPKPKDTLMI  300

SRTPEVTCVV VDVSQEDPEV QFNWYVDGVE VHNAKTKPRE EQFQSTYRVV SVLTVLHQDW  360

LNGKEYKCKV SNKGLPSSIE KTISKAKGQP REPQVYTLPP SQEEMTKNQV SLTCLVKGFY  420

PSDIAVEWES NGQPENNYKT TPPVLDSDGS FFLYSRLTVD KSRWQEGNVF SCSVMHEALH  480

NHYTQKSLSL SLGKFWVLVV VGGVLACYSL LVTVAFIIFW VRSKRSRLLH SDYMNMTPRR  540

PGPTRKHYQP YAPPRDFAAY RSKRGRKKLL YIFKQPFMRP VQTTQEEDGC SCRFPEEEEG  600

GCELRVKFSR SADAPAYKQG QNQLYNELNL GRREEYDVLD KRRGRDPEMG GKPRRKNPQE  660

GLYNELQKDK MAEAYSEIGM KGERRRGKGH DGLYQGLSTA TKDTYDALHM QALPPR       716
```

The coding DNA sequence of CAR-T20.20 (SEQ ID NO: 32) is as follows:

```
atggccttac cagtgaccgc cttgctcctg ccgctggcct tgctgctcca cgccgccagg     60

ccggaagtgc agctggtgga gtctggggga ggcttggtac agcctggcag gtccctgaga    120

ctctcctgtg cagcctctgg attcaccttt aatgattatg ccatgcactg ggtccggcaa    180

gctccaggga agggcctgga gtgggtctca actattagtt ggaatagtgg ttccataggc    240

tatgcggact ctgtgaaggg ccgattcacc atctccagag acaacgccaa gaagtccctg    300

tatctgcaaa tgaacagtct gagagctgag gacacggcct tgtattactg tgcaaaagat    360

atacagtacg gcaactacta ctacggtatg gacgtctggg gccaagggac cacggtcacc    420

gtctcctcag gtggcggtgg ctcgggcggt ggtgggtcgg gtggcggcgg atctgaaatt    480

gtgttgacac agtctccagc caccctgtct ttgtctccag ggaaagagc caccctctcc    540

tgcagggcca gtcagagtgt tagcagctac ttagcctggt accaacagaa acctggccag    600

gctcccaggc tcctcatcta tgatgcatcc aacagggcca ctggcatccc agccaggttc    660

agtggcagtg ggtctgggac agacttcact ctcaccatca gcagcctaga gcctgaagat    720

tttgcagttt attactgtca gcagcgtagc aactggccga tcaccttcgg ccaagggaca    780

cgactggaga ttaaagagag caagtacgga ccgccctgcc ccccttgccc tgcccccgag    840

ttcgagggcg gacccagcgt gttcctgttc ccccccaagc ccaaggacac cctgatgatc    900

agccggaccc ccgaggtgac ctgcgtggtg gtggacgtga gccaggaaga tcccgaggtc    960

cagttcaatt ggtacgtgga cggcgtggaa gtgcacaacg ccaagaccaa gcccagagag   1020

gaacagttcc aaagcaccta ccgggtggtg tctgtgctga ccgtgctgca ccaggactgg   1080

ctgaacggca aagaatacaa gtgcaaggtg tccaacaagg gcctgcccag cagcatcgaa   1140

aagaccatca gcaaggccaa gggccagcct cgcgagcccc aggtgtacac cctgcctccc   1200

tcccaggaag agatgaccaa gaaccaggtg tccctgacct gcctggtgaa gggcttctac   1260

cccagcgaca tcgccgtgga gtgggagagc aacggccagc ctgagaacaa ctacaagacc   1320

acccctcccg tgctggacag cgacggcagc ttcttcctgt acagccggct gaccgtggac   1380
```

-continued

```
aagagccggt ggcaggaagg caacgtcttt agctgcagcg tgatgcacga ggccctgcac    1440

aaccactaca cccagaagag cctgagcctg tccctgggca agttttgggt gctggtggtg    1500

gttggtggag tcctggcttg ctatagcttg ctagtaacag tggcctttat tattttctgg    1560

gtgaggagta agaggagcag gctcctgcac agtgactaca tgaacatgac tccccgccgc    1620

cccgggccca cccgcaagca ttaccagccc tatgccccac cacgcgactt cgcagcctat    1680

cgctccaaac ggggcagaaa gaaactcctg tatatattca aacaaccatt tatgagacca    1740

gtacaaacta ctcaagagga agatggctgt agctgccgat ttccagaaga agaagaagga    1800

ggatgtgaac tgagagtgaa gttcagcagg agcgcagacg cccccgcgta caagcagggc    1860

cagaaccagc tctataacga gctcaatcta ggacgaagag aggagtacga tgttttggac    1920

aagagacgtg gccgggaccc tgagatgggg ggaaagccga gaaggaagaa ccctcaggaa    1980

ggcctgtaca atgaactgca gaaagataag atggcggagg cctacagtga gattgggatg    2040

aaaggcgagc gccggagggg caaggggcac gatggccttt accagggtct cagtacagcc    2100

accaaggaca cctacgacgc ccttcacatg caggccctgc cccctcgcta a             2151
```

Antigen Binding Domain

In one embodiment, the CAR of the invention comprises a target-specific binding element referred to as antigen binding domain. The antigen binding domain of the CAR of the invention is a specific binding element targeting CD20.

In a preferred embodiment of the invention, the antigen binding domain comprises a heavy chain variable region and a light chain variable region of an anti-CD20 antibody.

In another preferred embodiment, the amino acid sequence of the heavy chain variable region of Ofatumumaband antibody is as follows:

```
                                                          (SEQ ID NO: 7)
EVQLVESGGG LVQPGRSLRL SCAASGFTFN DYAMHWVRQA PGKGLEWVST ISWNSGSIGY   60

ADSVKGRFTI SRDNAKKSLY LQMNSLRAED TALYYCAKDI QYGNYYYGMD VWGQGTTVTV  120

SS;                                                                122
```

and the DNA sequence encoding the heavy chain variable region of Ofatumumaband antibody is as follows:

```
                                                          (SEQ ID NO: 8)
GAAGTGCAGC TGGTGGAGTC TGGGGGAGGC TTGGTACAGC CTGGCAGGTC CCTGAGACTC     60

TCCTGTGCAG CCTCTGGATT CACCTTTAAT GATTATGCCA TGCACTGGGT CCGGCAAGCT    120

CCAGGGAAGG GCCTGGAGTG GGTCTCAACT ATTAGTTGGA ATAGTGGTTC CATAGGCTAT    180

GCGGACTCTG TGAAGGGCCG ATTCACCATC TCCAGAGACA ACGCCAAGAA GTCCCTGTAT    240

CTGCAAATGA ACAGTCTGAG AGCTGAGGAC ACGGCCTTGT ATTACTGTGC AAAAGATATA    300

CAGTACGGCA ACTACTACTA CGGTATGGAC GTCTGGGGCC AAGGGACCAC GGTCACCGTC    360

TCCTCA;                                                              366
```

or, the amino acid sequence of the heavy chain variable region of Rituximab antibody is as follows:

```
                                                          (SEQ ID NO: 9)
QVQLQQPGAE LVKPGASVKM SCKASGYTFT SYNMHWVKQT PGRGLEWIGA IYPGNGDTSY   60

NQKFKGKATL TADKSSSTAY MQLSSLTSED SAVYYCARST YYGGDWYFNV WGAGTTVTVS  120

A;                                                                 121
```

and the DNA sequence encoding the heavy chain variable region of Rituximab antibody is as follows:

```
                                                      (SEQ ID NO: 10)
CAGGTGCAGT TGCAACAGCC TGGAGCTGAG TTGGTGAAGC CTGGTGCTTC TGTGAAGATG   60

TCTTGTAAGG CTTCTGGATA CACATTCACT TCTTACAACA TGCACTGGGT GAAGCAGACT  120

CCTGGTAGGG GTTTGGAGTG GATCGGAGCT ATCTACCCAG GAAACGGAGA CACATCTTAC  180

AACCAGAAGT TCAAGGGTAA GGCTACATTG ACTGCTGACA AGTCTTCATC TACTGCTTAC  240

ATGCAATTGT CTTCTTTGAC ATCTGAGGAC TCTGCAGTTT ACTACTGCGC TAGGTCTACA  300

TACTACGGAG GTGACTGGTA CTTCAACGTG TGGGGAGCAG GTACCACGGT CACTGTCTCT  360

GCA.                                                               363
```

Further, the amino acid sequence of the heavy chain variable region of Obinutuzumab antibody used in the present invention is as follows:

```
                                                      (SEQ ID NO: 33)
QVQLVQSGAE VKKPGSSVKV SCKASGYAFS YSWINWVRQA PGQGLEWMGR IFPGDGDTDY   60

NGKFKGRVTI TADKSTSTAY MELSSLRSED TAVYYCARNV FDGYWLVYWG QGTLVTVSS   119
```

The DNA sequence encoding the heavy chain variable region of Obinutuzumab antibody is as follows:

```
                                                     (SEQ ID NO: 34)
caggtgcaat tggtgcagtc tggcgctgaa gttaagaagc ctgggagttc agtgaaggtc   60

tcctgcaagg cttccggata cgccttcagc tattcttgga tcaattgggt gcggcaggcg  120

cctggacaag ggctcgagtg gatgggacgg atctttcccg gcgatgggga tactgactac  180

aatgggaaat tcaagggcag agtcacaatt accgccgaca aatccactag cacagcctat  240

atggagctga gcagcctgag atctgaggac acggccgtgt attactgtgc aagaaatgtc  300

tttgatggtt actggcttgt ttactggggc cagggaaccc tggtcaccgt ctcctca     357
```

In another preferred embodiment, the amino acid sequence of the light chain variable region of Ofatumumaband antibody is as follows:

```
                                                      (SEQ ID NO: 11)
EIVLTQSPAT LSLSPGERAT LSCRASQSVS SYLAWYQQKP GQAPRLLIYD ASNRATGIPA   60

RFSGSGSGTD FTLTISSLEP EDFAVYYCQQ RSNWPITFGQ GTRLEIK               107
```

The DNA sequence of Ofatumumaband antibody is as follows:

```
                                                      (SEQ ID NO: 12)
GAAATTGTGT TGACACAGTC TCCAGCCACC CTGTCTTTGT CTCCAGGGGA AAGAGCCACC   60

CTCTCCTGCA GGGCCAGTCA GAGTGTTAGC AGCTACTTAG CCTGGTACCA ACAGAAACCT  120

GGCCAGGCTC CCAGGCTCCT CATCTATGAT GCATCCAACA GGGCCACTGG CATCCCAGCC  180

AGGTTCAGTG GCAGTGGGTC TGGGACAGAC TTCACTCTCA CCATCAGCAG CCTAGAGCCT  240

GAAGATTTTG CAGTTTATTA CTGTCAGCAG CGTAGCAACT GGCCGATCAC CTTCGGCCAA  300

GGGACACGAC TGGAGATTAA A                                            321
```

Alternatively, the amino acid sequence of the light chain variable region of Rituximab antibody is as follows:

```
                                                        (SEQ ID NO: 13)
QIVLSQSPAI LSASPGEKVT MTCRASSSVS YIHWFQQKPG SSPKPWIYAT SNLASGVPVR   60

FSGSGSGTSY SLTISRVEAE DAATYYCQQW TSNPPTFGGG TKLEIK                 106
```

The DNA sequences encoding the light chain (VL) of single-chain variable region derived from Rituximab antibody is:

```
                                                          (SEQ ID NO: 14)
CAAATTGTTC TCTCCCAGTC TCCAGCAATC CTGTCAGCTT CTCCTGGAGA GAAGGTGACT    60

ATGACTTGCA GGGCTTCTTC ATCTGTTTCT TACATCCACT GGTTCCAGCA GAAGCCTGGT   120

TCTTCACCTA AGCCTTGGAT CTACGCTACA TCTAACTTGG CATCTGGAGT GCCTGTGAGG   180

TTCTCTGGTT CTGGTTCAGG TACTTCTTAC TCTTTGACAA TCTCTAGGGT GGAGGCTGAG   240

GACGCTGCTA CTTACTACTG CCAGCAGTGG ACATCTAACC CTCCAACATT CGGAGGTGGT   300

ACTAAGTTGG AGATCAAG.                                                318
```

Further, the amino acid sequence of the light chain variable region of Obinutuzumab antibody used in the present invention is as follows:

```
                                                        (SEQ ID NO: 35)
DIVMTQTPLS LPVTPGEPAS ISCRSSKSLL HSNGITYLYW YLQKPGQSPQ LLIYQMSNLV   60

SGVPDRFSGS GSGTDFTLKI SRVEAEDVGV YYCAQNLELP YTFGGGTKVE IKRTV       115
```

The DNA sequence encoding the heavy chain variable region of Obinutuzumab antibody is as follows:

```
                                                        (SEQ ID NO: 36)
gatatcgtga tgacccagac tccactctcc ctgcccgtca cccctggaga gcccgccagc   60

attagctgca ggtctagcaa gagcctcttg cacagcaatg gcatcactta tttgtattgg  120

tacctgcaaa agccagggca gtctccacag ctcctgattt atcaaatgtc caaccttgtc  180

tctggcgtcc ctgaccggtt ctccggctcc gggtcaggca ctgatttcac actgaaaatc  240

agcagggtgg aggctgagga tgttggagtt tattactgcg ctcagaatct agaacttcct  300

tacaccttcg gcggagggac caaggtggag atcaaacgta cggtg                  345
```

In a preferred embodiment of the invention, the amino acid sequence of the linker between the heavy chain variable region and the light chain variable region is as follows:

```
                       (SEQ ID NO: 15)
GGGGSGGGGS GGGGS          15
```

and its coding DNA sequence is as follows:

```
                                          (SEQ ID NO: 16)
GGTGGCGGTG  GCTCGGGCGG  TGGTGGGTCG  GGTGGCGGCG  GATCT  45
```

Hinge Region and Transmembrane Region

As for the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some embodiments, transmembrane domains may be selected or modified by amino acid substitutions to avoid binding such domains to the transmembrane domain of the same or different surface membrane proteins, thereby minimizing the interaction with other members of the receptor complexes.

In a preferred embodiment of the invention, the hinge region comprises the following amino acid sequence (IgG4 Hinge-CH2-CH3 hinge region):

```
                                                   (SEQ ID NO: 17)
ESKYGPPCPP CPAPEFLGGP SVFLFPPKPK DTLMISRTPE VTCVVVDVSQ EDPEVQFNWY   60

VDGVEVHNAK TKPREEQFNS TYRVVSVLTV LHQDWLNGKE YKCKVSNKGL PSSIEKTISK  120

AKGQPREPQV YTLPPSQEEM TKNQVSLTCL VKGFYPSDIA VEWESNGQPE NNYKTTPPVL  180

DSDGSFFLYS RLTVDKSRWQ EGNVFSCSVM HEALHNHYTQ KSLSLSLGK              229
```

Its coding DNA sequence is as follows:

```
                                                     (SEQ ID NO: 18)
GAGAGCAAGT ACGGACCGCC CTGCCCCCCT TGCCCTGCCC CCGAGTTCCT GGGCGGACCC   60

AGCGTGTTCC TGTTCCCCCC CAAGCCCAAG GACACCCTGA TGATCAGCCG GACCCCCGAG  120

GTGACCTGCG TGGTGGTGGA CGTGAGCCAG GAAGATCCCG AGGTCCAGTT CAATTGGTAC  180

GTGGACGGCG TGGAAGTGCA CAACGCCAAG ACCAAGCCCA GAGAGGAACA GTTCAACAGC  240

ACCTACCGGG TGGTGTCTGT GCTGACCGTG CTGCACCAGG ACTGGCTGAA CGGCAAAGAA  300

TACAAGTGCA AGGTGTCCAA CAAGGGCCTG CCCAGCAGCA TCGAAAAGAC CATCAGCAAG  360

GCCAAGGGCC AGCCTCGCGA GCCCCAGGTG TACACCCTGC CTCCCTCCCA GGAAGAGATG  420

ACCAAGAACC AGGTGTCCCT GACCTGCCTG GTGAAGGGCT TCTACCCCAG CGACATCGCC  480

GTGGAGTGGG AGAGCAACGG CCAGCCTGAG AACAACTACA AGACCACCCC TCCCGTGCTG  540

GACAGCGACG GCAGCTTCTT CCTGTACAGC CGGCTGACCG TGGACAAGAG CCGGTGGCAG  600

GAAGGCAACG TCTTTAGCTG CAGCGTGATG CACGAGGCCC TGCACAACCA CTACACCCAG  660

AAGAGCCTGA GCCTGTCCCT GGGCAAG;                                     687
```

or, the hinge region comprises the following amino acid sequence (IgG4 Hinge-CH2-CH3 (L235E, N297Q)):

```
                                                     (SEQ ID NO: 19)
ESKYGPPCPP CPAPEFEGGP SVFLFPPKPK DTLMISRTPE VTCVVVDVSQ EDPEVQFNWY   60

VDGVEVHNAK TKPREEQFQS TYRVVSVLTV LHQDWLNGKE YKCKVSNKGL PSSIEKTISK  120

AKGQPREPQV YTLPPSQEEM TKNQVSLTCL VKGFYPSDIA VEWESNGQPE NNYKTTPPVL  180

DSDGSFFLYS RLTVDKSRWQ EGNVFSCSVM HEALHNHYTQ KSLSLSLGK              229
```

Its coding DNA sequence is as follows:

```
                                                     (SEQ ID NO: 20)
GAGAGCAAGT ACGGACCGCC CTGCCCCCCT TGCCCTGCCC CCGAGTTCGA GGGCGGACCC   60

AGCGTGTTCC TGTTCCCCCC CAAGCCCAAG GACACCCTGA TGATCAGCCG GACCCCCGAG  120

GTGACCTGCG TGGTGGTGGA CGTGAGCCAG GAAGATCCCG AGGTCCAGTT CAATTGGTAC  180

GTGGACGGCG TGGAAGTGCA CAACGCCAAG ACCAAGCCCA GAGAGGAACA GTTCCAAAGC  240

ACCTACCGGG TGGTGTCTGT GCTGACCGTG CTGCACCAGG ACTGGCTGAA CGGCAAAGAA  300

TACAAGTGCA AGGTGTCCAA CAAGGGCCTG CCCAGCAGCA TCGAAAAGAC CATCAGCAAG  360

GCCAAGGGCC AGCCTCGCGA GCCCCAGGTG TACACCCTGC CTCCCTCCCA GGAAGAGATG  420

ACCAAGAACC AGGTGTCCCT GACCTGCCTG GTGAAGGGCT TCTACCCCAG CGACATCGCC  480

GTGGAGTGGG AGAGCAACGG CCAGCCTGAG AACAACTACA AGACCACCCC TCCCGTGCTG  540

GACAGCGACG GCAGCTTCTT CCTGTACAGC CGGCTGACCG TGGACAAGAG CCGGTGGCAG  600
```

-continued

```
GAAGGCAACG TCTTTAGCTG CAGCGTGATG CACGAGGCCC TGCACAACCA CTACACCCAG 660

AAGAGCCTGA GCCTGTCCCT GGGCAAG.                                    687
```

In a preferred embodiment of the invention, the amino acid sequence of the transmembrane region derived from CD8 (CD8TM) is as follows:

```
                                    (SEQ ID NO: 21)
IYIWAPLAGT CGVLLLSLVI TLYC
                                               24
```

The coding DNA sequence thereof is as follows:

```
                                                      (SEQ ID NO: 22)
ATCTACATCT GGGCGCCCTT GGCCGGGACT TGTGGGGTCC TTCTCCTGTC ACTGGTTATC 60

ACCCTTTACT GC                                                     72
```

In a preferred embodiment of the invention, the amino acid sequence of the transmembrane region derived from CD28 (CD28TM) is as follows:

```
                                    (SEQ ID NO: 37)
FWVLVVVGGV LACYSLLVTV AFIIFWV;
                                               27
```

The DNA sequence encoding the transmembrane region derived from CD28 (CD28TM) is as follows:

```
                                                        (SEQ ID NO: 38)
TTTTGGGTGC TGGTGGTGGT TGGTGGAGTC CTGGCTTGCT ATAGCTTGCT AGTAACAGTG   60

GCCTTTATTA TTTTCTGGGT G.                                            81
```

Intracellular Domain

The intracellular domain in the CAR of the invention comprises the signaling domain of 4-1BB and the signaling domain of CD3ζ.

Preferably, the intracellular signaling domain of 4-1BB comprises the following amino acid sequence:

```
                                    (SEQ ID NO: 23)
KRGRKKLLYI FKQPFMRPVQ TTQEEDGCSC RFPEEEEGGC EL
                                                   42
```

The coding DNA sequence thereof is as follows:

```
                                                        (SEQ ID NO: 24)
AAACGGGGCA GAAAGAAACT CCTGTATATA TTCAAACAAC CATTTATGAG ACCAGTACAA  60

ACTACTCAAG AGGAAGATGG CTGTAGCTGC CGATTTCCAG AAGAAGAAGA AGGAGGATGT 120

GAACTG                                                            126
```

Preferably, the intracellular signaling domain derived from CD28 comprises the following amino acid sequence:

```
                                   (SEQ ID NO: 39)
RSKRSRLLHS DYMNMTPRRP GPTRKHYQPY APPRDFAAYR S  41
```

The coding DNA sequence thereof is as follows:

```
                                                     (SEQ ID NO: 40)
AGGAGTAAGA GGAGCAGGCT CCTGCACAGT GACTACATGA ACATGACTCC CCGCCGCCCC   60

GGGCCCACCC GCAAGCATTA CCAGCCCTAT GCCCCACCAC GCGACTTCGC AGCCTATCGC  120

TCC                                                                123
```

Preferably, the intracellular signaling domain of CD3ζ comprises the following amino acid sequence:

```
                                                      (SEQ ID NO: 25)
RVKFSRSADA PAYQQGQNQL YNELNLGRRE EYDVLDKRRG RDPEMGGKPQ RRKNPQEGLY     60

NELQKDKMAE AYSEIGMKGE RRRGKGHDGL YQGLSTATKD TYDALHMQAL PPR           113
```

The coding DNA sequence thereof is as follows:

```
                                                      (SEQ ID NO: 26)
AGAGTGAAGT TCAGCAGGAG CGCAGACGCC CCCGCGTACA AGCAGGGCCA GAACCAGCTC   60

TATAACGAGC TCAATCTAGG ACGAAGAGAG GAGTACGATG TTTTGGACAA GAGACGTGGC  120

CGGGACCCTG AGATGGGGGG AAAGCCGAGA AGGAAGAACC CTCAGGAAGG CCTGTACAAT  180

GAACTGCAGA AAGATAAGAT GGCGGAGGCC TACAGTGAGA TTGGGATGAA AGGCGAGCGC  240

CGGAGGGGCA AGGGGCACGA TGGCCTTTAC CAGGGTCTCA GTACAGCCAC CAAGGACACC  300

TACGACGCCC TTCACATGCA GGCCCTGCCC CCTCGC                            336
```

Vector

The invention also provides a DNA construct encoding the CAR sequences of the invention.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The present invention also provides vectors in which the DNA construct of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector, The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors, Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e g, mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In the case where a non-viral delivery system is utilized, genome editing technique is exemplarily employed to complete the invention, for example CRISPR-Cas9, ZFN or TALEN.

In a preferred embodiment of the invention, the vector is a lentiviral vector.

In a preferred embodiment of the invention, the DNA construct further comprises a signal peptide coding sequence. Preferably, the signal peptide sequence is ligated upstream of the nucleic acid sequence of antigen binding domain. Preferably the signal peptide is a human CD8a signal peptide.

Preferably, the amino acid sequence of the signal peptide is as follows:

The amino acid sequence of CD8 leader sequence is:

```
                                         (SEQ ID NO: 27)
MALPVTALLL PLALLLHAAR P                     21
```

The DNA sequence encoding CD8 leader sequence is:

```
                                                          (SEQ ID NO: 28)
ATGGCCTTAC CAGTGACCGC CTTGCTCCTG CCGCTGGCCT TGCTGCTCCA CGCCGCCAGG  60

CCG                                                                 63
```

Therapeutic Application

The present invention encompasses a cell (e.g., T cell) transduced with a lentiviral vector (LV) encoding the CAR of the invention. The transduced T cell can elicit a CAR-mediated T-cell response.

Thus, the present invention also provides a method for stimulating a T cell-mediated immune response to a target cell population or tissue in a mammal comprising the step of administering to the mammal a T cell that expresses the CAR of the invention.

In one embodiment, the present invention includes a type of cellular therapy where T cells are genetically modified to express the CAR of the invention and the CAR-T cell is infused to a recipient in need thereof. The infused cell is able to kill tumor cells in the recipient. Unlike antibody therapies, CAR-T cells are able to replicate in vivo resulting in long-term persistence that can lead to sustained tumor control.

In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-CD20 CAR-T cell elicits an immune response specific against cells expressing CD20.

Although the data disclosed herein specifically disclose lentiviral vector comprising anti-CD20 scFv, hinge and transmembrane domain, and 4-1BB and CD3ζ signaling domains, the invention should be construed to include any number of variations for each of the components of the construct as described elsewhere herein.

Adaptation diseases that may be treated include CD20 positive tumors and diseases caused by excessive B cells (such as autoimmune diseases, for example, lupus erythematosus, etc.). CD20 positive tumors may include CD20 positive non-solid tumors (such as hematological tumors, for example, leukemias and lymphomas) or solid tumors. Types of tumors or cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CCL. In certain embodiments, the cells of the invention are used in the treatment of patients at risk for developing CCL. Thus, the present invention provides methods for the treatment or prevention of CCL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. In general, $1\times10^6$ to $1\times10^{10}$ of the modified T cells of the invention (e.g., CAR-T 20 cells) can be applied to patients by means of, for example, intravenous infusion each treatment or each course of treatment.

The Advantages of the Present Invention Include (1) As for the chimeric antigen receptor of the present invention, the extracellular antigen binding domain thereof is a specific anti-CD20 scFv. The CAR formed by binding the specific anti-CD20 scFv to a specific hinge region and an intracellular domain shows a great capability of killing tumor cells with low cytotoxicity and low side effects.

(2) The chimeric antigen receptor provided by the invention can achieve stable expression and membrane localization of CAR protein after T cells is infected by lentivirus carrying CAR gene.

(3) The CAR-modified T cell of the present invention has a longer survival time in vivo and strong anti-tumor efficacy. The optimized CAR with the IgG4 Hinge-CH2-CH3 linker region can avoid the binding of the Fc receptor and the subsequent ADCC effect (antibody-dependent cytotoxicity).

Example 1 Construction of Lentiviral Expression Vector

The full-length DNA synthesis and cloning construction of coding plasmids were commissioned by Shanghai Boyi Biotechnology Co., Ltd. Different anti-CD20 scFv coding sequences were used in each plasmid. The cloning vector was selected as pWPT lentiviral vector. The cloning sites were BamH I and Sal I sites. The specific sequence structure is shown in FIG. 1. The amino acid and nucleotide sequences of each element are as described above.

In the following examples, CAR-T20.13, CAR-T20.14, CAR-T20.16, CAR-T20.19, CAR-T20.20 with better effects are taken as examples.

Example 2 Preparation of CAR-T Cell (1) After taking venous blood from healthy people, mononuclear cells (PBMCs) were isolated by density gradient centrifugation.

(2) On day 0, PBMCs were cultured in GT-T551 cell culture medium containing 2% human albumin, and the final concentration of cells was adjusted to $2\times10^6$ cells/mL. The cells were seeded in a cell culture flask previously coated with Retronectin (purchased from TAKARA) at a final concentration of 10 μg/mL and CD3 monoclonal antibody (OKT3) at a final concentration of 5 μg/mL. Recombinant human interleukin 2 (IL-2) was added to the culture medium at a final concentration of 1000 U/mL. The cells were cultured in an incubator with a saturated humidity and 5% $CO_2$ at 37° C.

(3) On day 2, fresh medium, concentrated and purified CAR20 lentivirus solution, protamine sulfate (12 μg/ml), and IL-2 (at a final concentration of 1000 U/mL) were added. After 12 hours of infection in a 5% $CO_2$ incubator at 37° C., the culture medium was discarded, fresh medium was added, and cultivation was continued in a 5% $CO_2$ incubator at 37° C.

(4) Starting from day 6, CART20 cells can be taken for the corresponding activity assay.

In the present invention, the preparation process of CAR-modified T cell targeting CD20 antigen is improved, and GT-551 serum-free medium supplemented with 2% human albumin was selected to culture lymphocytes in vitro.

Figure 2A:
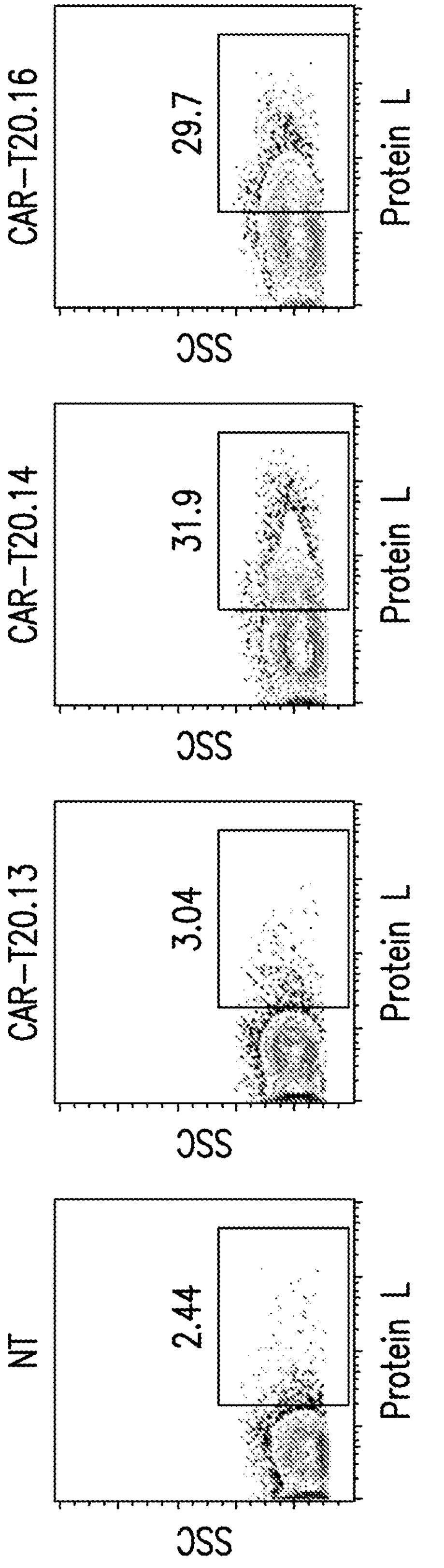
FIGS. 2A and 2B show detection of transfection efficiency of engineered T cell with chimeric antigen receptors targeting CD20. The expression level of the CAR gene-encoded protein on the surface of the T cell membrane in CAR-T20s cells cultured on day 7 (FIG. 2A) and day 11 (FIG. 2B) was identified by the Protein L method.
Figure 2B:
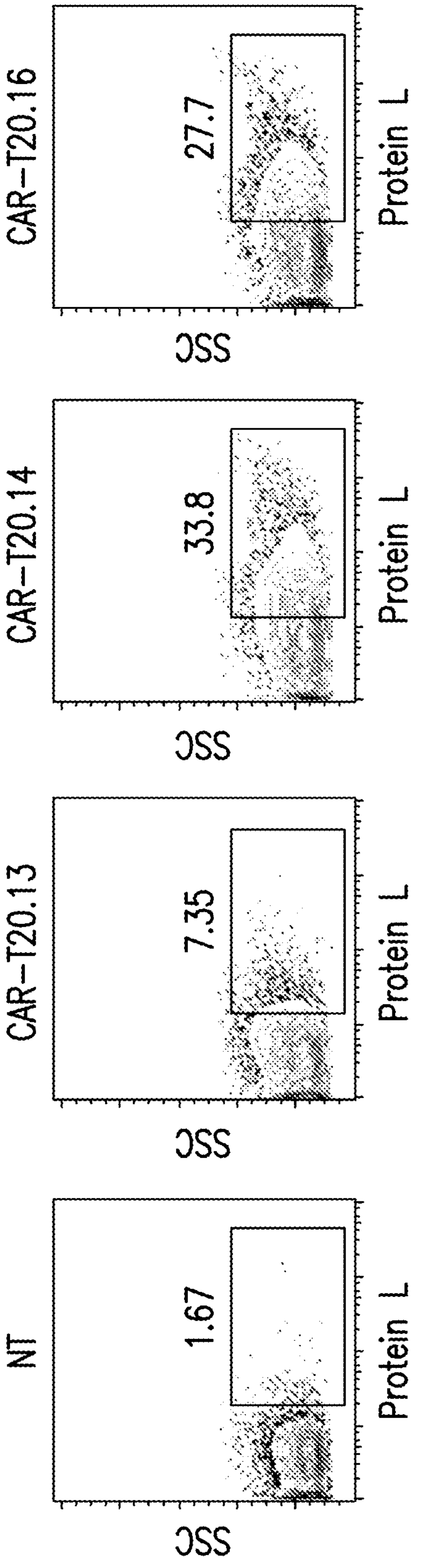
Figure 5A:
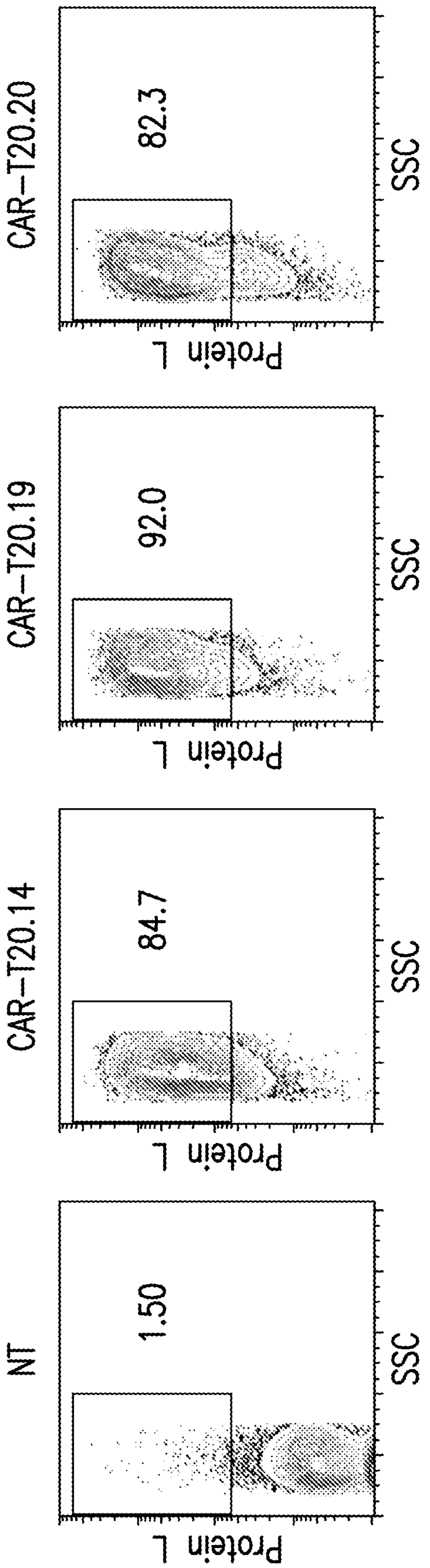
FIGS. 5A-5C show identification of the activation ability in vitro of the third generation chimeric antigen receptor and the chimeric antigen receptor with mutation in hinge region (which are constructed based on the sequence of Ofatumumaband antibody). The expression level of the CAR gene-encoded protein (FIG. 5A) on the surface of the T cell membrane in CAR-T20.14, CAR-T20.19 and CAR-T20.20 cells cultured on day 7 was identified by the Protein L method. $1*10^5$ of NT, CART-20.14, CART-20.19 and CAR-T20.20 cells (cultured on day 7) were cultured respectively with K562, K562 stable transfected cells of CD19 single positive, CD20 single positive, CD19 and CD20 double positive, and RAH target cell in 200 μl GT-551 medium for 18 h in a ratio of 1:1. Then the expression level of CD137 on the surface of T cell membrane (FIG. 5B) and the secretion level of IFNγ in the culture supernatant (FIG. 5C) were detected, respectively.

Example 3 Detection of the Integration Rate of the CAR Gene in the T Cell Genome and the Expression Level of the Encoded Protein Thereof on the Membrane Surface $0.5\times10^6$ of CART-20 cell samples cultured on day 7 (FIG. 2A and FIG. 5A) and day 11 (FIG. 2B) in Example 2 were taken, respectively. The expression level of CAR20 protein on the surface of T cell membrane was analyzed by flow cytometry after Protein L staining. The results showed that, except for CAR-T20.13, all of the CAR structures designed in this study can detect the chimeric antigen receptor localization on the cell membrane surface of the corresponding modified T cells using Protein L.

Example 4 Detection of the In Vitro Activation Ability of CAR-T20s

Figure 3A:
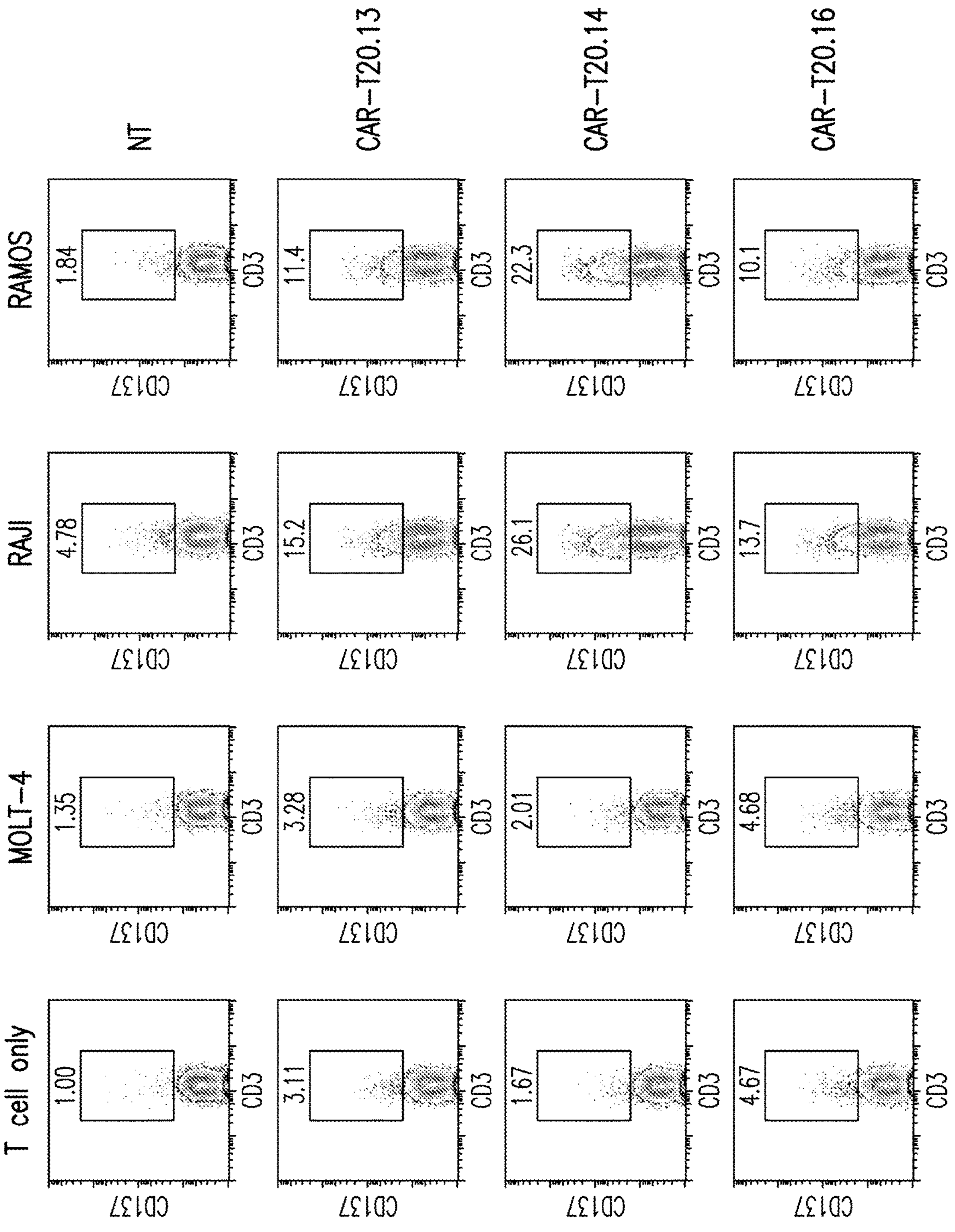
FIGS. 3A and 3B. $1*10^5$ of NT, CART-20.13, CART-20.14 and CAR-T20.16 cells (cultured on day 6) were co-cultured respectively with CD20-positive RAJI and RAMOS tumor cell lines, and CD20-negative MOLT-4 tumor cell line in 200 μl GT-551 medium for 18 h in a ratio of 1:1. Then the expression level of CD137 on the surface of T cell membrane (FIG. 3A) and the secretion level of IFNγ in the co-culture supernatant (FIG. 3B) were detected.
Figure 3B:
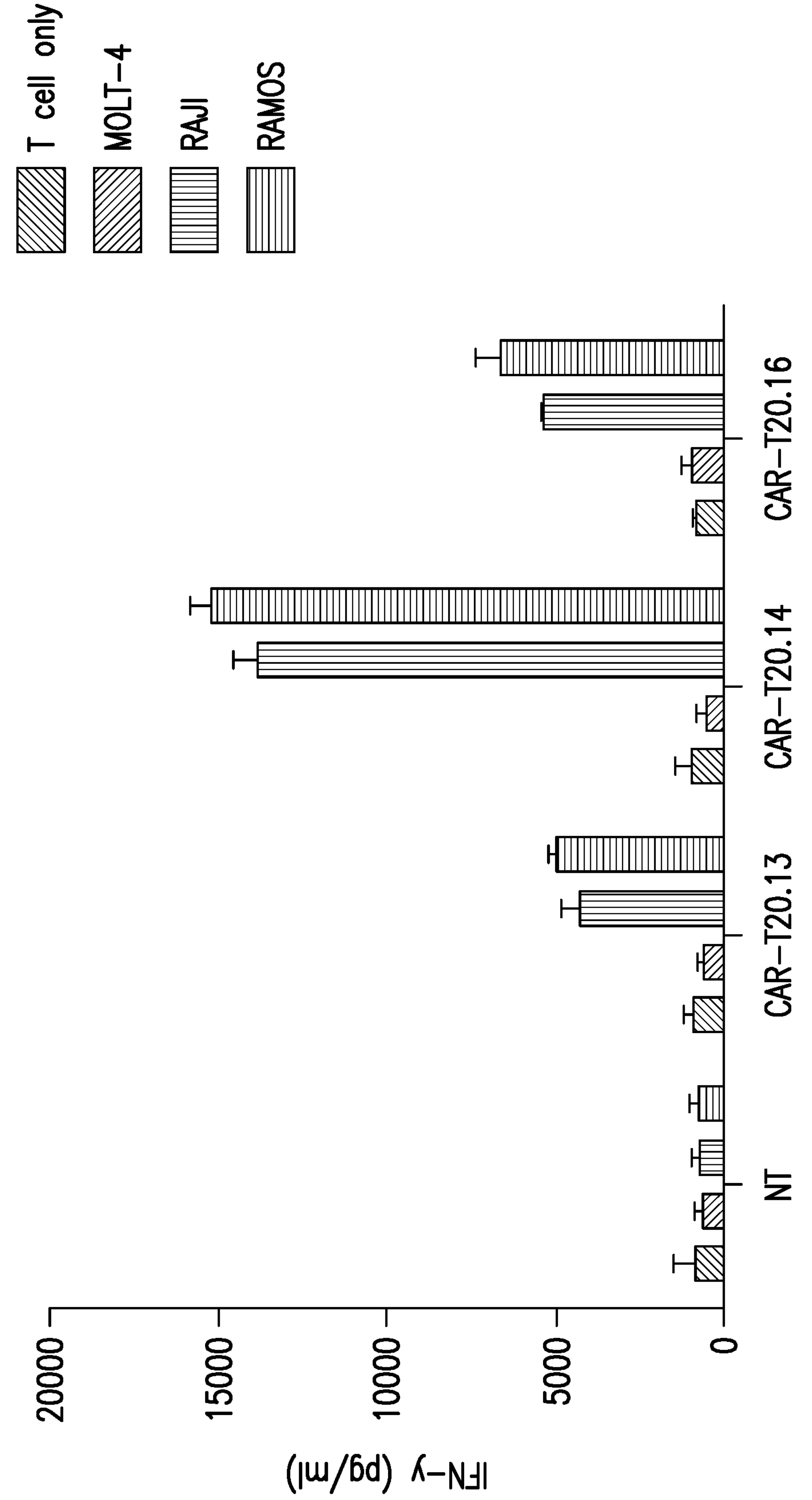

The deCAR-T20 cells cultured on day 6 in Example 2 were co-cultured with target cells. Then the up-regulated level of CD137 and the secretion level of IFNγ in the culture supernatant were examined $1\times10^5$ of CART-20 cells (cultured on day 6) were cultured respectively with CD20-positive RAJI and RAMOS tumor cell lines, and CD20-negative MOLT-4 tumor cell line, or without tumor cells, in 200 μl GT-551 medium for 18 h in a ratio of 1:1. Then the expression level of CD137 on the surface of T cell membrane was detected by flow cytometry (FIG. 3A) and the secretion level of IFNγ in the culture supernatant was detected by ELISA (FIG. 3B).

From the results in FIG. 3, we could concluded that the CAR based on Obinutuzumab also achieved expression and membrane surface localization in the corresponding modified cells, but the CAR structure based on the Ofatumumab sequence showed better in vitro activation ability and specificity targeting antigen when compared with the CAR constructed based on Obinutuzumab and Rituximab.

Example 5 Detection of the CAR-T20s Cells Induced Early Apoptosis Activity of Tumor Cells CART-20.13, CART-20.14 and CAR-T20.16 cells (cultured on day 11) from Example 2 were co-cultured respectively with $1\times10^4$ of CFSE-labeled CD20-negative (MOLT-4) or CD20-positive (RAJI, RAMOS) tumor cell lines in 200 μl GT-551 medium for 4 h. Then the cell pellet was collected by centrifugation. The cells were washed twice with PBS and stained for 30 min with Annexin V-APC dye in a ratio of 1:50 in 100 μl of dyeing solution. After washing with PBSonce, the proportion of Annexin V positive cells in CFSE positive cells was analyzed on a flow cytometry.

Figure 4:
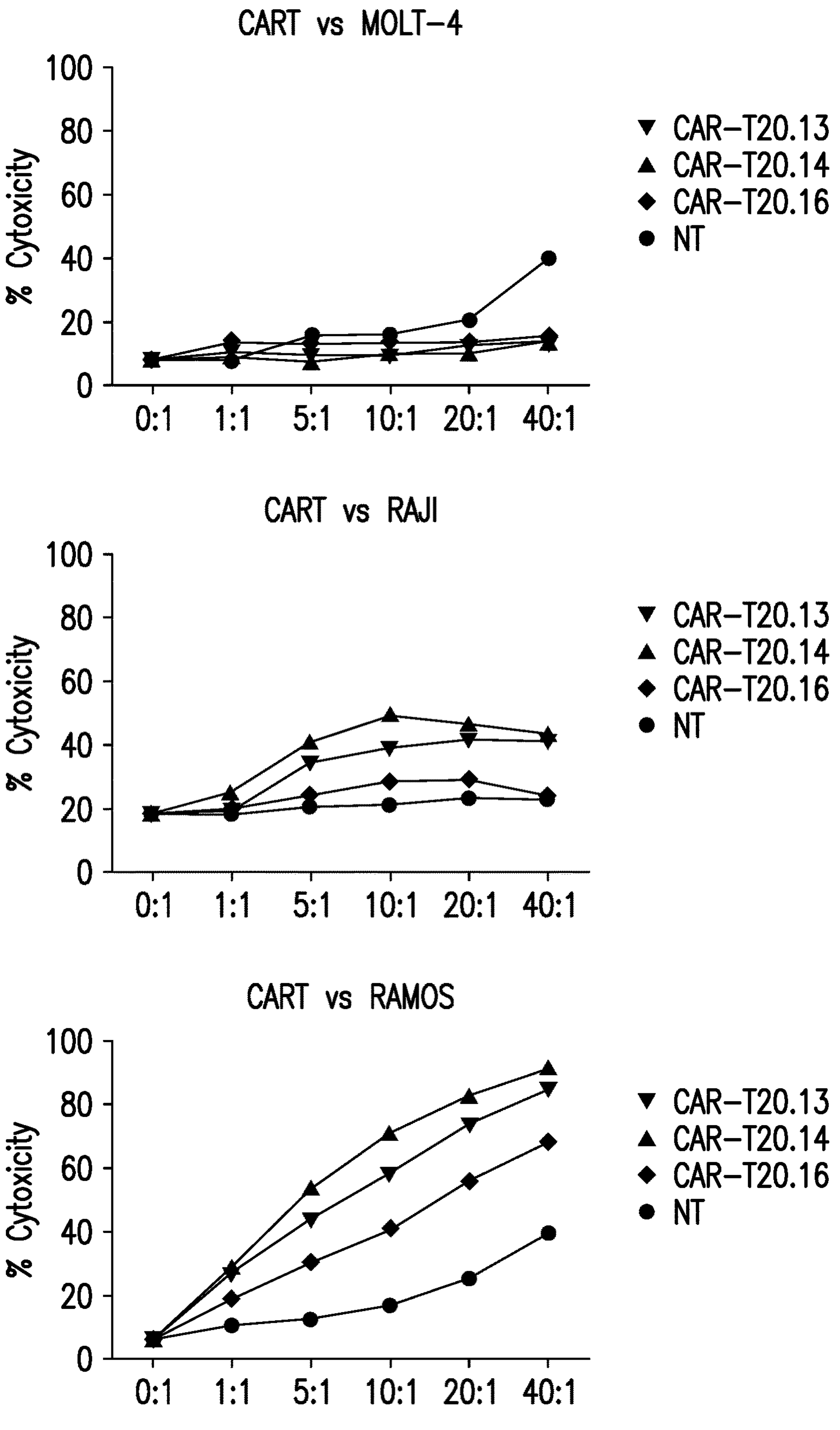
FIG. 4 shows detection of apoptosis levels of tumor cells induced by CART-20. $1*10^4$ of CFSE-labeled CD20-negative (MOLT-4) or CD20-positive (RAJI, RAMOS) tumor cell lines were co-cultured respectively with NT, CART-20.13, CART-20.14 and CAR-T20.16 cells (cultured on day 11) in 200 μl GT-551 medium for 4 h according to the ratio as shown in figure. Then the cell pellet was collected by centrifugation. The cells were washed twice with PBS and stained for 30 min with Annexin V-APC dye in a ratio of 1:50 in 100 μl of dyeing solution. After washing with PBS for 1 time, the proportion of Annexin V positive cells in CFSE positive cells was analyzed on a flow cytometry. The results in figure show the statistical analysis of Annexin V positive cells in the corresponding co-culture samples.

The results in FIG. 4 show that the CAR structure based on the Ofatumumab sequence shows better ability to induce early apoptosis of CD20 target cells in vitro when compared with the CAR constructed based on Obinutuzumab and Rituximab.

Figure 5B:
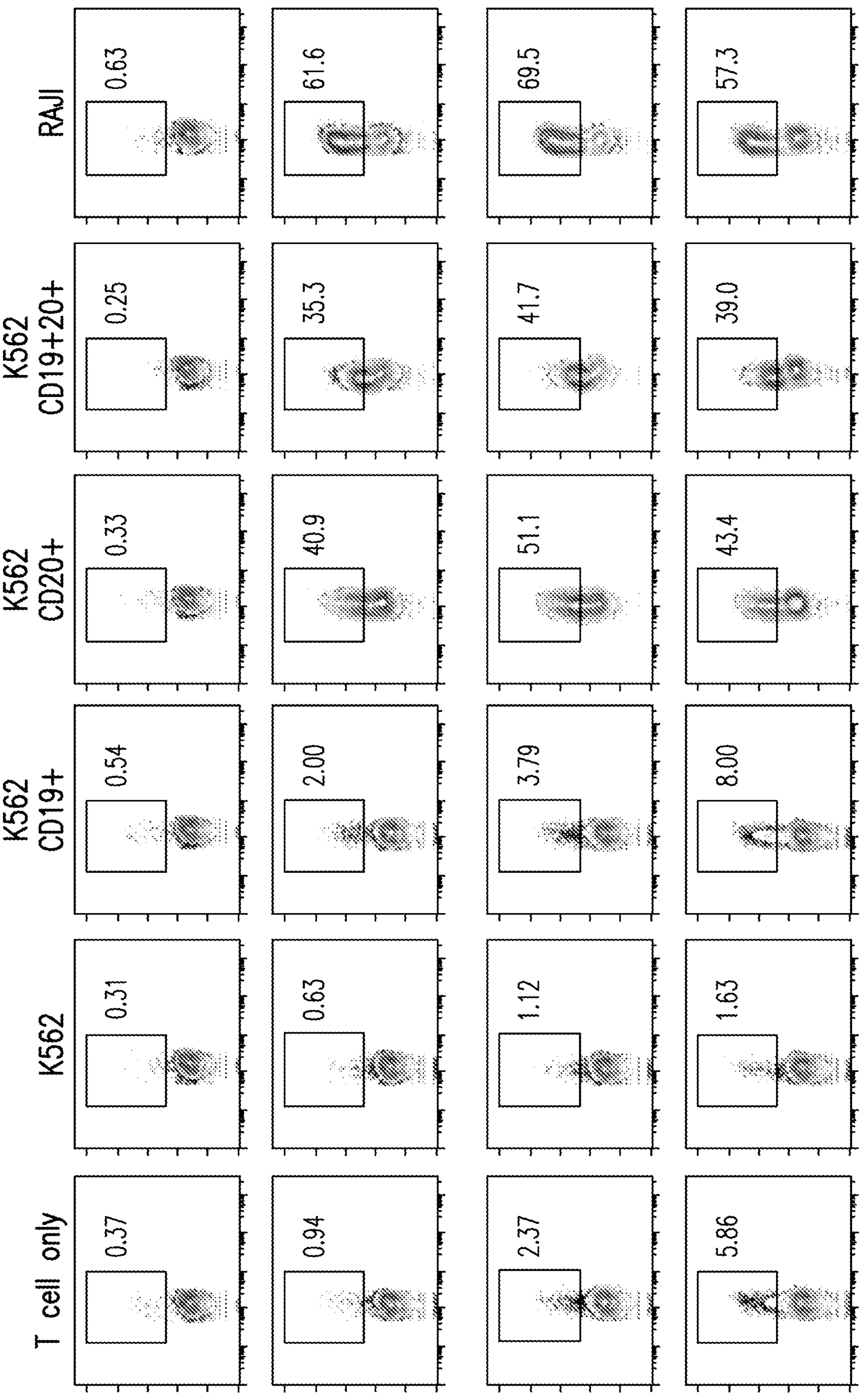
Figure 5C:
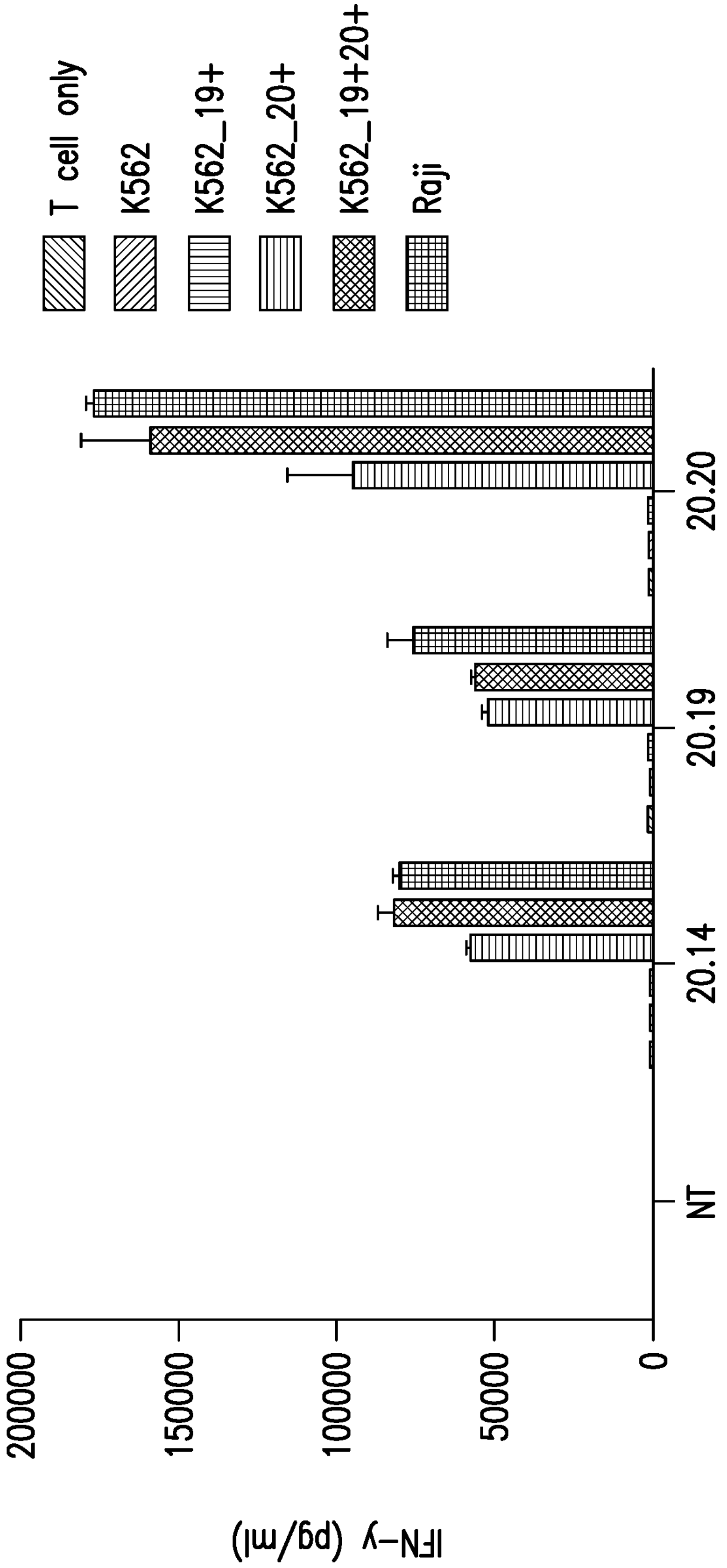

Example 6 Identification of the In Vitro Activation Ability of the Third Generation Chimeric Antigen Receptor and the Chimeric Antigen Receptor with Mutation in Hinge Region (1) Under the condition that the transfection rate was basically equal (FIG. 5A), the CAR-T20s cells (prepared by the method of Example 2) cultured on the day 7 were cultured respectively with K562, K562 stable transfected cells of CD19 single positive, CD20 single positive, CD19 and CD20 double positive, and RAJI target cell (each taking $1\times10^5$ cells) in 200 μl GT-551 medium for 18 h in a ratio of 1:1. Then the up-regulated level of CD137 (FIG. 5B) and the secretion level of IFNγ in the culture supernatant (FIG. 5C) were detected.

(2) The results shown in FIG. 5 indicate that the in vitro activation ability (CD137 and IFNg) of the chimeric antigen receptor CAR-T20.14 and CAR-T20.19 (having a mutation in the hinge region) is substantially equivalent, in the case of substantially identical infection efficiency. The third generation CAR structure CAR-T20.20 shows better in vitro activation capacity (CD137 and IFNγ) than the second generation CAR-T20.14 and CAR-T20.19.

Example 7. Detection of the Ability of CAR-T20 Cells to Scavenge CD20 Positive Cells In Vivo (1) Raji-Luc cells expressing luciferase were injected into NCG mice ($5\times10^5$/mouse) through the tail vein. One week after the inoculation, the in vivo expansion of the tumor cells was observed by in vivo imaging and recorded as Day 0. NT and CAR-T20.19 cells were injected into Day 0 mice ($5\times10^6$/mouse) through the tail vein. On Day0, Day7, Day14, Day21, the expansion of tumor cells in mice was observed by in vivo imaging and analyzed based on changes in fluorescence intensity and body weight changes of mice.

Figure 6:
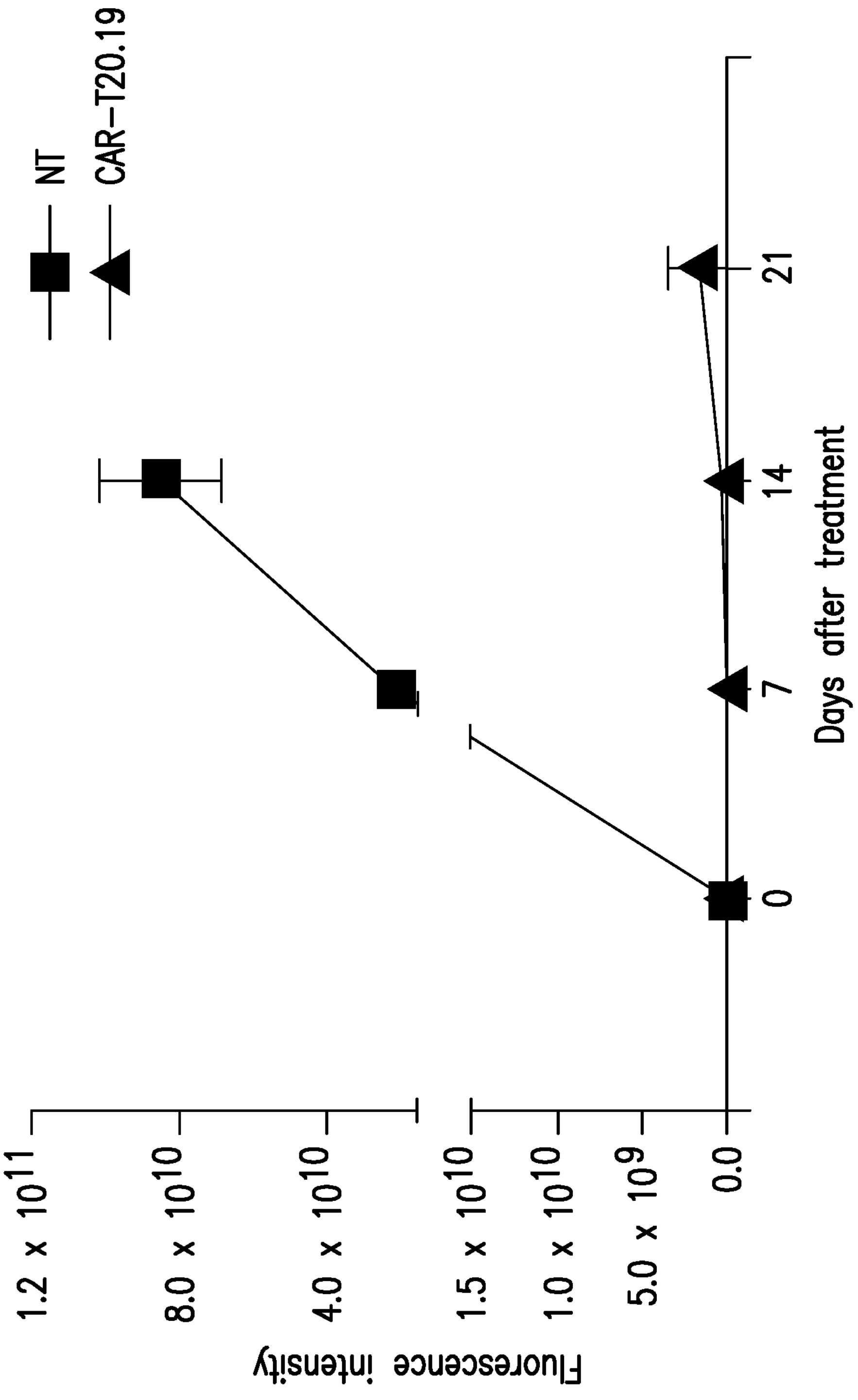
FIG. 6 shows the detection results of the ability of CAR-T20 cells to scavenge CD20-positive cells in vivo. The results indicate that CAR-T20.19 can effectively inhibit the in vivo expansion of CD20-positive tumor cells.

(2) The results shown in FIG. 6 indicate that CAR-T20.19 can effectively inhibit the in vivo expansion of CD20-positive tumor cells.

The preferred embodiments of the present invention are described in detail above, but the present invention is not limited to the specific details in above embodiments. Various simple modifications can be made to the technical solutions of the present invention within the scope of the technical idea of the present invention. These simple variants all fall within the protection scope of the present invention.

It should be further noted that the specific technical features described in the above specific embodiments may be combined in any suitable manner without contradiction. To avoid unnecessary repetition, the various possible combinations of the invention are not described separately.

In addition, any combination of various embodiments of the invention may be made as long as it does not deviate from the idea of the invention, and it should be regarded as the disclosure of the invention.

The invention claimed is:

1. An immune cell comprising a chimeric antigen receptor (CAR), the CAR comprising an anti-CD20 antigen binding region which comprises: (i) a heavy chain variable region ($V_H$) having the amino acid sequence set forth as SEQ ID NO: 7, and (ii) a light chain variable region ($V_L$) having the amino acid sequence set forth as SEQ ID NO: 11;

wherein the anti-CD20 antigen-binding region is a single-chain variable fragment (scFv) that specifically binds CD20, wherein the CAR further comprises:

(iv) a hinge region having an amino acid sequence encoded by a nucleic acid sequence having ≥90% identity to the nucleic acid sequence set forth as SEQ ID NO: 20, (v) a transmembrane domain having an amino acid sequence encoded by a nucleic acid sequence having ≥90% identity to the nucleic acid sequence set forth as SEQ ID NO: 22, (vi) a co-stimulatory region having an amino acid sequence encoded by a nucleic acid sequence having ≥90% identity to the nucleic acid sequence set forth as SEQ ID NO: 24, and (vii) a cytoplasmic signaling domain having an amino acid sequence encoded by a nucleic acid sequence having ≥90% identity to the nucleic acid sequence set forth as SEQ ID NO: 26; and wherein the CAR comprises, from N-terminus to C-terminus: $V_H$, $V_L$, the hinge region, the transmembrane domain, the co-stimulatory region, and the cytoplasmic signaling domain.

2. The immune cell of claim 1, wherein the immune cell is a T cell.

3. An immune cell comprising a chimeric antigen receptor (CAR), the CAR comprising an anti-CD20 antigen binding region which comprises: (i) a heavy chain variable region ($V_H$) having the amino acid sequence set forth as SEQ ID NO: 7, and (ii) a light chain variable region ($V_L$) having the amino acid sequence set forth as SEQ ID NO: 11;

wherein $V_H$ is located at the N-terminus of $V_L$, wherein the anti-CD20 antigen-binding region is a single-chain variable fragment (scFv) that specifically binds CD20, and wherein the CAR comprises an amino acid sequence encoded by a nucleic acid sequence having ≥95% identity to the nucleic acid sequence set forth as SEQ ID NO: 6.

4. The immune cell of claim 3, wherein the CAR comprises an amino acid sequence encoded by a nucleic acid sequence having ≥98% identity to the nucleic acid sequence set forth as SEQ ID NO: 6.

5. The immune cell of claim 3, wherein the immune cell is a T cell.

6. A pharmaceutical composition comprising an immune cell of claim 3 and a pharmaceutically acceptable carrier.

7. The pharmaceutical composition of claim 6, wherein the CAR comprises an amino acid sequence encoded by a nucleic acid sequence having ≥95% identity to the nucleic acid sequence set forth as SEQ ID NO: 6.

8. The pharmaceutical composition of claim 6, wherein the CAR comprises an amino acid sequence encoded by a nucleic acid sequence having ≥98% identity to the nucleic acid sequence set forth as SEQ ID NO: 6.

9. The pharmaceutical composition of claim 6, wherein the immune cell is a T cell.

* * * * *

SEQUENCE LISTING

```
Sequence total quantity: 40
SEQ ID NO: 1            moltype = AA  length = 672
FEATURE                 Location/Qualifiers
REGION                  1..672
                        note = CAR
source                  1..672
                        mol_type = protein
                        organism = synthetic construct
SEQUENCE: 1
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGGGGSGG GGSGGGGSEI VLTQSPATLS LSPGERATLS  180
CRASQSVSSY LAWYQQKPGQ APRLLIYDAS NRATGIPARF SGSGSGTDFT LTISSLEPED  240
FAVYYCQQRS NWPITFGQGT RLEIKESKYG PPCPPCPAPE FLGGPSVFLF PPKPKDTLMI  300
SRTPEVTCVV VDVSQEDPEV QFNWYVDGVE VHNAKTKPRE EQFNSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKIYIWAP LAGTCGVLLL SLVITLYCKR GRKKLLYIFK QPFMRPVQTT  540
QEEDGCSCRF PEEEEGGCEL RVKFSRSADA PAYKQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                     672

SEQ ID NO: 2            moltype = DNA  length = 2019
FEATURE                 Location/Qualifiers
misc_feature            1..2019
                        note = CAR
source                  1..2019
                        mol_type = other DNA
                        organism = synthetic construct
SEQUENCE: 2
atggccttac cagtgaccgc cttgctcctg ccgctggcct tgctgctcca cgccgccagg  60
ccggaagtgc agctggtgga gtctggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gtggcggtgg ctcgggcggt ggtgggtcgg gtggcggcgg atctgaaatt  480
gtgttgacac agtctccagc caccctgtct ttgtctccag gggaaagagc caccctctcc  540
tgcagggcca gtcagagtgt tagcagctac ttagcctggt accaacagaa acctggccag  600
gctcccaggc tcctcatcta tgatgcatcc aacagggcca ctggcatccc agccaggttc  660
agtggcagtg ggtctgggac agacttcact ctcaccatca gcagcctaga gcctgaagat  720
tttgcagttt attactgtca gcagcgtagc aactggccga tcaccttcgg ccaagggaca  780
cgactggaga ttaaagagag caagtacgga ccgccctgcc ccccttgccc tgcccccgag  840
ttcctgggcg gacccagcgt gttcctgttc cccccccaagc ccaaggacac cctgatgatc  900
agccggaccc ccgaggtgac ctgcgtggtg gtggacgtga gccaggaaga tcccgaggtc  960
cagttcaatt ggtacgtgga cggcgtggaa gtgcacaacg ccaagaccaa gcccagagag  1020
gaacagttca acagcaccta ccgggtggtg tctgtgctga ccgtgctgca ccaggactgg  1080
ctgaacggca aagaatacaa gtgcaaggtg tccaacaagg gcctgcccag cagcatcgaa  1140
aagaccatca gcaaggccaa gggccagcct cgcgagcccc aggtgtacac cctgcctccc  1200
tcccaggaag agatgaccaa gaaccaggtg tccctgacct gcctggtgaa gggcttctac  1260
cccagcgaca tcgccgtgga gtgggagagc aacggccagc ctgagaacaa ctacaagacc  1320
acccctcccg tgctggacag cgacggcagc ttcttcctgt acagccggct gaccgtggac  1380
aagagccggt ggcaggaagg caacgtcttt agctgcagcg tgatgcacga ggccctgcac  1440
aaccactaca cccagaagag cctgagcctg tccctgggca agatctacat ctgggcgccc  1500
ttggccggga cttgtggggt ccttctcctg tcactggtta tcacccttta ctgcaaacgg  1560
ggcagaaaga aactcctgta tatattcaaa caaccattta tgagaccagt acaaactact  1620
caagaggaag atggctgtag ctgccgattt ccagaagaag aagaaggagg atgtgaactg  1680
agagtgaagt tcagcaggag cgcagacgcc cccgcgtaca agcagggcca gaaccagctc  1740
tataacgagc tcaatctagg acgaagagag gagtacgatg ttttggacaa gagacgtggc  1800
cgggaccctg agatgggggg aaagccgaga aggaagaacc ctcaggaagg cctgtacaat  1860
gaactgcaga aagataagat ggcggaggcc tacagtgaga ttgggatgaa aggcgagcgc  1920
cggaggggca aggggcacga tggcctttac cagggtctca gtacagccac caaggacacc  1980
tacgacgccc ttcacatgca ggccctgccc cctcgctag                        2019

SEQ ID NO: 3            moltype = AA  length = 670
FEATURE                 Location/Qualifiers
REGION                  1..670
                        note = CAR
source                  1..670
                        mol_type = protein
                        organism = synthetic construct
SEQUENCE: 3
MALPVTALLL PLALLLHAAR PQVQLQQPGA ELVKPGASVK MSCKASGYTF TSYNMHWVKQ  60
TPGRGLEWIG AIYPGNGDTS YNQKFKGKAT LTADKSSSTA YMQLSSLTSE DSAVYYCARS  120
TYYGGDWYFN VWGAGTTVTV SAGGGGSGGG GSGGGGSQIV LSQSPAILSA SPGEKVTMTC  180
RASSSVSYIH WFQQKPGSSP KPWIYATSNL ASGVPVRFSG SGSGTSYSLT ISRVEAEDAA  240
TYYCQQWTSN PPTFGGGTKL EIKESKYGPP CPPCPAPEFL GGPSVFLFPP KPKDTLMISR  300
```

```
TPEVTCVVVD VSQEDPEVQF NWYVDGVEVH NAKTKPREEQ FNSTYRVVSV LTVLHQDWLN  360
GKEYKCKVSN KGLPSSIEKT ISKAKGQPRE PQVYTLPPSQ EEMTKNQVSL TCLVKGFYPS  420
DIAVEWESNG QPENNYKTTP PVLDSDGSFF LYSRLTVDKS RWQEGNVFSC SVMHEALHNH  480
YTQKSLSLSL GKIYIWAPLA GTCGVLLLSL VITLYCKRGR KKLLYIFKQP FMRPVQTTQE  540
EDGCSCRFPE EEEGGCELRV KFSRSADAPA YKQGQNQLYN ELNLGRREEY DVLDKRRGRD  600
PEMGGKPRRK NPQEGLYNEL QKDKMAEAYS EIGMKGERRR GKGHDGLYQG LSTATKDTYD  660
ALHMQALPPR                                                        670

SEQ ID NO: 4           moltype = DNA  length = 2013
FEATURE                Location/Qualifiers
misc_feature           1..2013
                       note = CAR
source                 1..2013
                       mol_type = other DNA
                       organism = synthetic construct
SEQUENCE: 4
atggccttac cagtgaccgc cttgctcctg ccgctggcct tgctgctcca cgccgccagg  60
ccgcaggtgc agttgcaaca gcctggagct gagttggtga agcctggtgc ttctgtgaag  120
atgtcttgta aggcttctgg atacacattc acttcttaca acatgcactg ggtgaagcag  180
actcctggta ggggtttgga gtggatcgga gctatctacc caggaaacgg agacacatct  240
tacaaccaga agttcaaggg taaggctaca ttgactgctg acaagtcttc atctactgct  300
tacatgcaat tgtcttcttt gacatctgag gactctgcag tttactactg cgctaggtct  360
acatactacg gaggtgactg gtacttcaac gtgtggggag caggtaccac ggtcactgtc  420
tctgcaggtg gaggtggatc tggaggagga ggatctggtg gaggaggttc tcaaattgtt  480
ctctcccagt ctccagcaat cctgtcagct tctcctggag agaaggtgac tatgacttgc  540
agggcttctt catctgtttc ttacatccac tggttccagc agaagcctgg ttcttcacct  600
aagccttgga tctacgctac atctaacttg gcatctggag tgcctgtgag gttctctggt  660
tctggttcag gtacttctta ctctttgaca atctctaggg tggaggctga ggacgctgct  720
acttactact gccagcagtg gacatctaac cctccaacat tcggaggtgg tactaagttg  780
gagatcaagg agagcaagta cggaccgccc tgcccccctt gccctgcccc cgagttcctg  840
ggcggaccca gcgtgttcct gttccccccc aagcccaagg acaccctgat gatcagccgg  900
acccccgagg tgacctgcgt ggtggtggac gtgagccagg aagatcccga ggtccagttc  960
aattggtacg tggacggcgt ggaagtgcac aacgccaaga ccaagcccag agaggaacag  1020
ttcaacagca cctaccgggt ggtgtctgtg ctgaccgtgc tgcaccagga ctggctgaac  1080
ggcaaagaat acaagtgcaa ggtgtccaac aagggcctgc ccagcagcat cgaaaagacc  1140
atcagcaagg ccaagggcca gcctcgcgag ccccaggtgt acaccctgcc tccctcccag  1200
gaagagatga ccaagaacca ggtgtccctg acctgcctgg tgaagggctt ctaccccagc  1260
gacatcgccg tggagtggga gagcaacggc cagcctgaga acaactacaa gaccacccct  1320
cccgtgctgg acagcgacgg cagcttcttc ctgtacagcc ggctgaccgt ggacaagagc  1380
cggtggcagg aaggcaacgt ctttagctgc agcgtgatgc acgaggccct gcacaaccac  1440
tacacccaga agagcctgag cctgtccctg ggcaagatct acatctgggc gcccttggcc  1500
gggacttgtg gggtccttct cctgtcactg gttatcaccc tttactgcaa acggggcaga  1560
aagaaactcc tgtatatatt caaacaacca tttatgagac cagtacaaac tactcaagag  1620
gaagatggct gtagctgccg atttccagaa gaagaagaag gaggatgtga actgagagtg  1680
aagttcagca ggagcgcaga cgcccccgcg tacaagcagg gccagaacca gctctataac  1740
gagctcaatc taggacgaag agaggagtac gatgttttgg acaagagacg tggccgggac  1800
cctgagatgg ggggaaagcc gagaaggaag aaccctcagg aaggcctgta caatgaactg  1860
cagaaagata agatggcgga ggcctacagt gagattggga tgaaaggcga gcgccggagg  1920
ggcaaggggc acgatggcct ttaccagggt ctcagtacag ccaccaagga cacctacgac  1980
gcccttcaca tgcaggccct gccccctcgc tag                              2013

SEQ ID NO: 5           moltype = AA  length = 672
FEATURE                Location/Qualifiers
REGION                 1..672
                       note = CAR
source                 1..672
                       mol_type = protein
                       organism = synthetic construct
SEQUENCE: 5
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGGGGSGG GGSGGGGSEI VLTQSPATLS LSPGERATLS  180
CRASQSVSSY LAWYQQKPGQ APRLLIYDAS NRATGIPARF SGSGSGTDFT LTISSLEPED  240
FAVYYCQQRS NWPITFGQGT RLEIKESKYG PPCPPCPAPE FEGGPSVFLF PPKPKDTLMI  300
SRTPEVTCVV VDVSQEDPEV QFNWYVDGVE VHNAKTKPRE EQFQSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKIYIWAP LAGTCGVLLL SLVITLYCKR GRKKLLYIFK QPFMRPVQTT  540
QEEDGCSCRF PEEEEGGCEL RVKFSRSADA PAYKQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                     672

SEQ ID NO: 6           moltype = DNA  length = 2019
FEATURE                Location/Qualifiers
misc_feature           1..2019
                       note = CAR
source                 1..2019
                       mol_type = other DNA
                       organism = synthetic construct
```

```
SEQUENCE: 6
atggccttac cagtgaccgc cttgctcctg ccgctggcct tgctgctcca cgccgccagg  60
ccggaagtgc agctggtgga gtctggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gtggcggtgg ctcgggcggt ggtgggtcgg gtggcggcgg atctgaaatt  480
gtgttgacac agtctccagc caccctgtct ttgtctccag gggaaagagc caccctctcc  540
tgcagggcca gtcagagtgt tagcagctac ttagcctggt accaacagaa acctggccag  600
gctcccaggc tcctcatcta tgatgcatcc aacagggcca ctggcatccc agccaggttc  660
agtggcagtg ggtctgggac agacttcact ctcaccatca gcagcctaga gcctgaagat  720
tttgcagttt attactgtca gcagcgtagc aactggccga tcaccttcgg ccaagggaca  780
cgactggaga ttaaagagag caagtacgga ccgccctgcc ccccttgccc tgcccccgag  840
ttcgagggcg gacccagcgt gttcctgttc ccccccaagc ccaaggacac cctgatgatc  900
agccggaccc ccgaggtgac ctgcgtggtg gtggacgtga gccaggaaga tcccgaggtc  960
cagttcaatt ggtacgtgga cggcgtggaa gtgcacaacg ccaagaccaa gcccagagag  1020
gaacagttcc aaagcaccta ccgggtggtg tctgtgctga ccgtgctgca ccaggactgg  1080
ctgaacggca aagaatacaa gtgcaaggtg tccaacaagg gcctgcccag cagcatcgaa  1140
aagaccatca gcaaggccaa gggccagcct cgcgagcccc aggtgtacac cctgcctccc  1200
tcccaggaag agatgaccaa gaaccaggtg tccctgacct gcctggtgaa gggcttctac  1260
cccagcgaca tcgccgtgga gtgggagagc aacggccagc ctgagaacaa ctacaagacc  1320
acccctcccg tgctggacag cgacggcagc ttcttcctgt acagccggct gaccgtggac  1380
aagagccggt ggcaggaagg caacgtcttt agctgcagcg tgatgcacga ggccctgcac  1440
aaccactaca cccagaagag cctgagcctg tccctgggca agatctacat ctgggcgccc  1500
ttggccggga cttgtggggt ccttctcctg tcactggtta tcacccttta ctgcaaacgg  1560
ggcagaaaga aactcctgta tatattcaaa caaccattta tgagaccagt acaaactact  1620
caagaggaag atggctgtag ctgccgattt ccagaagaag aagaaggagg atgtgaactg  1680
agagtgaagt tcagcaggag cgcagacgcc cccgcgtaca agcagggcca gaaccagctc  1740
tataacgagc tcaatctagg acgaagagag gagtacgatg ttttggacaa gagacgtggc  1800
cgggaccctg agatgggggg aaagccgaga aggaagaacc ctcaggaagg cctgtacaat  1860
gaactgcaga aagataagat ggcggaggcc tacagtgaga ttgggatgaa aggcgagcgc  1920
cggaggggca aggggcacga tggcctttac cagggtctca gtacagccac caaggacacc  1980
tacgacgccc ttcacatgca ggccctgccc cctcgctag                         2019

SEQ ID NO: 7           moltype = AA  length = 122
FEATURE                Location/Qualifiers
REGION                 1..122
                       note = Heavy chain variable region (VH)
source                 1..122
                       mol_type = protein
                       organism = synthetic construct
SEQUENCE: 7
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                                 122

SEQ ID NO: 8           moltype = DNA  length = 366
FEATURE                Location/Qualifiers
misc_feature           1..366
                       note = Heavy chain variable region (VH)
source                 1..366
                       mol_type = other DNA
                       organism = synthetic construct
SEQUENCE: 8
gaagtgcagc tggtggagtc tgggggaggc ttggtacagc ctggcaggtc cctgagactc  60
tcctgtgcag cctctggatt cacctttaat gattatgcca tgcactgggt ccggcaagct  120
ccagggaagg gcctggagtg ggtctcaact attagttgga atagtggttc cataggctat  180
gcggactctg tgaagggccg attcaccatc tccagagaca acgccaagaa gtccctgtat  240
ctgcaaatga acagtctgag agctgaggac acggccttgt attactgtgc aaaagatata  300
cagtacggca actactacta cggtatggac gtctggggcc aagggaccac ggtcaccgtc  360
tcctca                                                             366

SEQ ID NO: 9           moltype = AA  length = 121
FEATURE                Location/Qualifiers
REGION                 1..121
                       note = Heavy chain variable region (VH)
source                 1..121
                       mol_type = protein
                       organism = synthetic construct
SEQUENCE: 9
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
A                                                                  121

SEQ ID NO: 10          moltype = DNA  length = 363
FEATURE                Location/Qualifiers
misc_feature           1..363
```

```
                          note = Heavy chain variable region (VH)
source                    1..363
                          mol_type = other DNA
                          organism = synthetic construct
SEQUENCE: 10
caggtgcagt tgcaacagcc tggagctgag ttggtgaagc ctggtgcttc tgtgaagatg  60
tcttgtaagg cttctggata cacattcact tcttacaaca tgcactgggt gaagcagact  120
cctggtaggg gtttggagtg gatcggagct atctacccag gaaacggaga cacatcttac  180
aaccagaagt tcaagggtaa ggctacattg actgctgaca agtcttcatc tactgcttac  240
atgcaattgt cttctttgac atctgaggac tctgcagttt actactgcgc taggtctaca  300
tactacggag gtgactggta cttcaacgtg tggggagcag gtaccacggt cactgtctct  360
gca                                                                 363

SEQ ID NO: 11             moltype = AA  length = 107
FEATURE                   Location/Qualifiers
REGION                    1..107
                          note = Light chain variable region (VL)
source                    1..107
                          mol_type = protein
                          organism = synthetic construct
SEQUENCE: 11
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK                 107

SEQ ID NO: 12             moltype = DNA  length = 321
FEATURE                   Location/Qualifiers
misc_feature              1..321
                          note = Light chain variable region (VL)
source                    1..321
                          mol_type = other DNA
                          organism = synthetic construct
SEQUENCE: 12
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgatcac cttcggccaa  300
gggacacgac tggagattaa a                                             321

SEQ ID NO: 13             moltype = AA  length = 106
FEATURE                   Location/Qualifiers
REGION                    1..106
                          note = Light chain variable region (VL)
source                    1..106
                          mol_type = protein
                          organism = synthetic construct
SEQUENCE: 13
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIK                  106

SEQ ID NO: 14             moltype = DNA  length = 318
FEATURE                   Location/Qualifiers
misc_feature              1..318
                          note = Light chain variable region (VL)
source                    1..318
                          mol_type = other DNA
                          organism = synthetic construct
SEQUENCE: 14
caaattgttc tctcccagtc tccagcaatc ctgtcagctt ctcctggaga gaaggtgact  60
atgacttgca gggcttcttc atctgtttct tacatccact ggttccagca gaagcctggt  120
tcttcaccta agccttggat ctacgctaca tctaacttgg catctggagt gcctgtgagg  180
ttctctggtt ctggttcagg tacttcttac tctttgacaa tctctagggt ggaggctgag  240
gacgctgcta cttactactg ccagcagtgg acatctaacc ctccaacatt cggaggtggt  300
actaagttgg agatcaag                                                 318

SEQ ID NO: 15             moltype = AA  length = 15
FEATURE                   Location/Qualifiers
REGION                    1..15
                          note = Linker Peptide
source                    1..15
                          mol_type = protein
                          organism = synthetic construct
SEQUENCE: 15
GGGGSGGGGS GGGGS                                                    15

SEQ ID NO: 16             moltype = DNA  length = 45
FEATURE                   Location/Qualifiers
misc_feature              1..45
                          note = Linker Peptide
```

```
source                  1..45
                        mol_type = other DNA
                        organism = synthetic construct
SEQUENCE: 16
ggtggcggtg gctcgggcgg tggtgggtcg ggtggcggcg gatct                45

SEQ ID NO: 17           moltype = AA  length = 229
FEATURE                 Location/Qualifiers
REGION                  1..229
                        note = Hinge region (H)
source                  1..229
                        mol_type = protein
                        organism = synthetic construct
SEQUENCE: 17
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 18           moltype = DNA  length = 687
FEATURE                 Location/Qualifiers
misc_feature            1..687
                        note = Hinge region (H)
source                  1..687
                        mol_type = other DNA
                        organism = synthetic construct
SEQUENCE: 18
gagagcaagt acggaccgcc ctgcccccct tgccctgccc ccgagttcct gggcggaccc  60
agcgtgttcc tgttcccccc caagcccaag gacaccctga tgatcagccg gacccccgag  120
gtgacctgcg tggtggtgga cgtgagccag gaagatcccg aggtccagtt caattggtac  180
gtggacggcg tggaagtgca caacgccaag accaagccca gagaggaaca gttcaacagc  240
acctaccggg tggtgtctgt gctgaccgtg ctgcaccagg actggctgaa cggcaaagaa  300
tacaagtgca aggtgtccaa caagggcctg cccagcagca tcgaaaagac catcagcaag  360
gccaagggcc agcctcgcga gccccaggtg tacaccctgc ctccctccca ggaagagatg  420
accaagaacc aggtgtccct gacctgcctg gtgaagggct tctaccccag cgacatcgcc  480
gtggagtggg agagcaacgg ccagcctgag aacaactaca agaccacccc tcccgtgctg  540
gacagcgacg gcagcttctt cctgtacagc cggctgaccg tggacaagag ccggtggcag  600
gaaggcaacg tctttagctg cagcgtgatg cacgaggccc tgcacaacca ctacacccag  660
aagagcctga gcctgtccct gggcaag                                    687

SEQ ID NO: 19           moltype = AA  length = 229
FEATURE                 Location/Qualifiers
REGION                  1..229
                        note = Hinge region (H)
source                  1..229
                        mol_type = protein
                        organism = synthetic construct
SEQUENCE: 19
ESKYGPPCPP CPAPEFEGGP SVFLFPPKPK DTLMISRTPE VTCVVVDVSQ EDPEVQFNWY  60
VDGVEVHNAK TKPREEQFQS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 20           moltype = DNA  length = 687
FEATURE                 Location/Qualifiers
misc_feature            1..687
                        note = Hinge region (H)
source                  1..687
                        mol_type = other DNA
                        organism = synthetic construct
SEQUENCE: 20
gagagcaagt acggaccgcc ctgcccccct tgccctgccc ccgagttcga gggcggaccc  60
agcgtgttcc tgttcccccc caagcccaag gacaccctga tgatcagccg gacccccgag  120
gtgacctgcg tggtggtgga cgtgagccag gaagatcccg aggtccagtt caattggtac  180
gtggacggcg tggaagtgca caacgccaag accaagccca gagaggaaca gttccaaagc  240
acctaccggg tggtgtctgt gctgaccgtg ctgcaccagg actggctgaa cggcaaagaa  300
tacaagtgca aggtgtccaa caagggcctg cccagcagca tcgaaaagac catcagcaag  360
gccaagggcc agcctcgcga gccccaggtg tacaccctgc ctccctccca ggaagagatg  420
accaagaacc aggtgtccct gacctgcctg gtgaagggct tctaccccag cgacatcgcc  480
gtggagtggg agagcaacgg ccagcctgag aacaactaca agaccacccc tcccgtgctg  540
gacagcgacg gcagcttctt cctgtacagc cggctgaccg tggacaagag ccggtggcag  600
gaaggcaacg tctttagctg cagcgtgatg cacgaggccc tgcacaacca ctacacccag  660
aagagcctga gcctgtccct gggcaag                                    687

SEQ ID NO: 21           moltype = AA  length = 24
FEATURE                 Location/Qualifiers
REGION                  1..24
                        note = Transmembrane domain (TM)
source                  1..24
```

```
                        mol_type = protein
                        organism = synthetic construct
SEQUENCE: 21
IYIWAPLAGT CGVLLLSLVI TLYC                                    24

SEQ ID NO: 22           moltype = DNA  length = 72
FEATURE                 Location/Qualifiers
misc_feature            1..72
                        note = Transmembrane domain (TM)
source                  1..72
                        mol_type = other DNA
                        organism = synthetic construct
SEQUENCE: 22
atctacatct gggcgccctt ggccgggact tgtggggtcc ttctcctgtc actggttatc  60
accctttact gc                                                 72

SEQ ID NO: 23           moltype = AA  length = 42
FEATURE                 Location/Qualifiers
REGION                  1..42
                        note = Co-stimulatory molecule (CS)
source                  1..42
                        mol_type = protein
                        organism = synthetic construct
SEQUENCE: 23
KRGRKKLLYI FKQPFMRPVQ TTQEEDGCSC RFPEEEEGGC EL                42

SEQ ID NO: 24           moltype = DNA  length = 126
FEATURE                 Location/Qualifiers
misc_feature            1..126
                        note = Co-stimulatory molecule (CS)
source                  1..126
                        mol_type = other DNA
                        organism = synthetic construct
SEQUENCE: 24
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                        126

SEQ ID NO: 25           moltype = AA  length = 113
FEATURE                 Location/Qualifiers
REGION                  1..113
                        note = CD3zeta
source                  1..113
                        mol_type = protein
                        organism = synthetic construct
SEQUENCE: 25
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR        113

SEQ ID NO: 26           moltype = DNA  length = 336
FEATURE                 Location/Qualifiers
misc_feature            1..336
                        note = CD3zeta
source                  1..336
                        mol_type = other DNA
                        organism = synthetic construct
SEQUENCE: 26
agagtgaagt tcagcaggag cgcagacgcc cccgcgtaca agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                       336

SEQ ID NO: 27           moltype = AA  length = 21
FEATURE                 Location/Qualifiers
REGION                  1..21
                        note = Leader (L)
source                  1..21
                        mol_type = protein
                        organism = synthetic construct
SEQUENCE: 27
MALPVTALLL PLALLLHAAR P                                       21

SEQ ID NO: 28           moltype = DNA  length = 63
FEATURE                 Location/Qualifiers
misc_feature            1..63
                        note = Leader (L)
source                  1..63
```

```
                         mol_type = other DNA
                         organism = synthetic construct
SEQUENCE: 28
atggccttac cagtgaccgc cttgctcctg ccgctggcct tgctgctcca cgccgccagg  60
ccg                                                                63

SEQ ID NO: 29            moltype = AA  length = 677
FEATURE                  Location/Qualifiers
REGION                   1..677
                         note = CAR
source                   1..677
                         mol_type = protein
                         organism = synthetic construct
SEQUENCE: 29
MALPVTALLL PLALLLHAAR PQVQLVQSGA EVKKPGSSVK VSCKASGYAF SYSWINWVRQ  60
APGQGLEWMG RIFPGDGDTD YNGKFKGRVT ITADKSTSTA YMELSSLRSE DTAVYYCARN  120
VFDGYWLVYW GQGTLVTVSS GGGGSGGGGS GGGGSDIVMT QTPLSLPVTP GEPASISCRS  180
SKSLLHSNGI TYLYWYLQKP GQSPQLLIYQ MSNLVSGVPD RFSGSGSGTD FTLKISRVEA  240
EDVGVYYCAQ NLELPYTFGG GTKVEIKRTV ESKYGPPCPP CPAPEFLGGP SVFLFPPKPK  300
DTLMISRTPE VTCVVVDVSQ EDPEVQFNWY VDGVEVHNAK TKPREEQFNS TYRVVSVLTV  360
LHQDWLNGKE YKCKVSNKGL PSSIEKTISK AKGQPREPQV YTLPPSQEEM TKNQVSLTCL  420
VKGFYPSDIA VEWESNGQPE NNYKTTPPVL DSDGSFFLYS RLTVDKSRWQ EGNVFSCSVM  480
HEALHNHYTQ KSLSLSLGKI YIWAPLAGTC GVLLLSLVIT LYCKRGRKKL LYIFKQPFMR  540
PVQTTQEEDG CSCRFPEEEE GGCELRVKFS RSADAPAYKQ GQNQLYNELN LGRREEYDVL  600
DKRRGRDPEM GGKPRRKNPQ EGLYNELQKD KMAEAYSEIG MKGERRRGKG HDGLYQGLST  660
ATKDTYDALH MQALPPR                                                 677

SEQ ID NO: 30            moltype = DNA  length = 2034
FEATURE                  Location/Qualifiers
misc_feature             1..2034
                         note = CAR
source                   1..2034
                         mol_type = other DNA
                         organism = synthetic construct
SEQUENCE: 30
atggccttac cagtgaccgc cttgctcctg ccgctggcct tgctgctcca cgccgccagg  60
ccgcaggtgc aattggtgca gtctggcgct gaagttaaga agcctgggag ttcagtgaag  120
gtctcctgca aggcttccgg atacgccttc agctattctt ggatcaattg ggtgcggcag  180
gcgcctggac aagggctcga gtggatggga cggatctttc ccggcgatgg ggatactgac  240
tacaatggga aattcaaggg cagagtcaca attaccgccg acaaatccac tagcacagcc  300
tatatggagc tgagcagcct gagatctgag gacacggccg tgtattactg tgcaagaaat  360
gtctttgatg gttactggct tgtttactgg ggccagggaa ccctggtcac cgtctcctca  420
ggtggcggtg gctcgggcgg tggtgggtcg ggtggcggcg gatctgatat cgtgatgacc  480
cagactccac tctccctgcc cgtcacccct ggagagcccg ccagcattag ctgcaggtct  540
agcaagagcc tcttgcacag caatggcatc acttatttgt attggtacct gcaaaagcca  600
gggcagtctc cacagctcct gatttatcaa atgtccaacc ttgtctctgg cgtccctgac  660
cggttctccg gctccgggtc aggcactgat ttcacactga aaatcagcag ggtggaggct  720
gaggatgttg gagtttatta ctgcgctcag aatctagaac ttccttacac cttcggcgga  780
gggaccaagg tggagatcaa acgtacggtg gagagcaagt acggaccgcc ctgcccccct  840
tgccctgccc ccgagttcct gggcggaccc agcgtgttcc tgttcccccc caagcccaag  900
gacaccctga tgatcagccg gacccccgag gtgacctgcg tggtggtgga cgtgagccag  960
gaagatcccg aggtccagtt caattggtac gtggacggcg tggaagtgca caacgccaag  1020
accaagccca gagaggaaca gttcaacagc acctaccggg tggtgtctgt gctgaccgtg  1080
ctgcaccagg actggctgaa cggcaaagaa tacaagtgca aggtgtccaa caagggcctg  1140
cccagcagca tcgaaaagac catcagcaag gccaagggcc agcctcgcga gccccaggtg  1200
tacaccctgc ctccctccca ggaagagatg accaagaacc aggtgtccct gacctgcctg  1260
gtgaagggct tctaccccag cgacatcgcc gtggagtggg agagcaacgg ccagcctgag  1320
aacaactaca agaccacccc tcccgtgctg gacagcgacg gcagcttctt cctgtacagc  1380
cggctgaccg tggacaagag ccggtggcag gaaggcaacg tctttagctg cagcgtgatg  1440
cacgaggccc tgcacaacca ctacacccag aagagcctga gcctgtccct gggcaagatc  1500
tacatctggg cgcccttggc cgggacttgt ggggtccttc tcctgtcact ggttatcacc  1560
ctttactgca aacggggcag aaagaaactc ctgtatatat tcaaacaacc atttatgaga  1620
ccagtacaaa ctactcaaga ggaagatggc tgtagctgcc gatttccaga agaagaagaa  1680
ggaggatgtg aactgagagt gaagttcagc aggagcgcag acgcccccgc gtacaagcag  1740
ggccagaacc agctctataa cgagctcaat ctaggacgaa gagaggagta cgatgttttg  1800
gacaagagac gtggccggga ccctgagatg gggggaaagc cgagaaggaa gaaccctcag  1860
gaaggcctgt acaatgaact gcagaaagat aagatggcgg aggcctacag tgagattggg  1920
atgaaaggcg agcgccggag gggcaagggg cacgatggcc tttaccaggg tctcagtaca  1980
gccaccaagg acacctacga cgcccttcac atgcaggccc tgccccctcg ctag        2034

SEQ ID NO: 31            moltype = AA  length = 716
FEATURE                  Location/Qualifiers
REGION                   1..716
                         note = CAR
source                   1..716
                         mol_type = protein
                         organism = synthetic construct
SEQUENCE: 31
MALPVTALLL PLALLLHAAR PEVQLVESGG GLVQPGRSLR LSCAASGFTF NDYAMHWVRQ  60
```

-continued

```
APGKGLEWVS TISWNSGSIG YADSVKGRFT ISRDNAKKSL YLQMNSLRAE DTALYYCAKD  120
IQYGNYYYGM DVWGQGTTVT VSSGGGGSGG GGSGGGGSEI VLTQSPATLS LSPGERATLS  180
CRASQSVSSY LAWYQQKPGQ APRLLIYDAS NRATGIPARF SGSGSGTDFT LTISSLEPED  240
FAVYYCQQRS NWPITFGQGT RLEIKESKYG PPCPPCPAPE FEGGPSVFLF PPKPKDTLMI  300
SRTPEVTCVV VDVSQEDPEV QFNWYVDGVE VHNAKTKPRE EQFQSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKFWVLVV VGGVLACYSL LVTVAFIIFW VRSKRSRLLH SDYMNMTPRR  540
PGPTRKHYQP YAPPRDFAAY RSKRGRKKLL YIFKQPFMRP VQTTQEEDGC SCRFPEEEEG  600
GCELRVKFSR SADAPAYKQG QNQLYNELNL GRREEYDVLD KRRGRDPEMG GKPRRKNPQE  660
GLYNELQKDK MAEAYSEIGM KGERRRGKGH DGLYQGLSTA TKDTYDALHM QALPPR      716

SEQ ID NO: 32          moltype = DNA  length = 2151
FEATURE                Location/Qualifiers
misc_feature           1..2151
                       note = CAR
source                 1..2151
                       mol_type = other DNA
                       organism = synthetic construct
SEQUENCE: 32
atggccttac cagtgaccgc cttgctcctg ccgctggcct tgctgctcca cgccgccagg  60
ccggaagtgc agctggtgga gtctggggga ggcttggtac agcctggcag gtccctgaga  120
ctctcctgtg cagcctctgg attcaccttt aatgattatg ccatgcactg ggtccggcaa  180
gctccaggga agggcctgga gtgggtctca actattagtt ggaatagtgg ttccataggc  240
tatgcggact ctgtgaaggg ccgattcacc atctccagag acaacgccaa gaagtccctg  300
tatctgcaaa tgaacagtct gagagctgag gacacggcct tgtattactg tgcaaaagat  360
atacagtacg gcaactacta ctacggtatg gacgtctggg gccaagggac cacggtcacc  420
gtctcctcag gtggcggtgg ctcgggcggt ggtgggtcgg gtggcggcgg atctgaaatt  480
gtgttgacac agtctccagc caccctgtct ttgtctccag gggaaagagc caccctctcc  540
tgcagggcca gtcagagtgt tagcagctac ttagcctggt accaacagaa acctggccag  600
gctcccaggc tcctcatcta tgatgcatcc aacagggcca ctggcatccc agccaggttc  660
agtggcagtg ggtctgggac agacttcact ctcaccatca gcagcctaga gcctgaagat  720
tttgcagttt attactgtca gcagcgtagc aactggccga tcaccttcgg ccaagggaca  780
cgactggaga ttaaagagag caagtacgga ccgccctgcc ccccttgccc tgcccccgag  840
ttcgagggcg gacccagcgt gttcctgttc ccccccaagc ccaaggacac cctgatgatc  900
agccggaccc ccgaggtgac ctgcgtggtg gtggacgtga gccaggaaga tcccgaggtc  960
cagttcaatt ggtacgtgga cggcgtggaa gtgcacaacg ccaagaccaa gcccagagag  1020
gaacagttcc aaagcaccta ccgggtggtg tctgtgctga ccgtgctgca ccaggactgg  1080
ctgaacggca aagaatacaa gtgcaaggtg tccaacaagg gcctgcccag cagcatcgaa  1140
aagaccatca gcaaggccaa gggccagcct cgcgagcccc aggtgtacac cctgcctccc  1200
tcccaggaag agatgaccaa gaaccaggtg tccctgacct gcctggtgaa gggcttctac  1260
cccagcgaca tcgccgtgga gtgggagagc aacggccagc ctgagaacaa ctacaagacc  1320
acccctcccg tgctggacag cgacggcagc ttcttcctgt acagccggct gaccgtggac  1380
aagagccggt ggcaggaagg caacgtcttt agctgcagcg tgatgcacga ggccctgcac  1440
aaccactaca cccagaagag cctgagcctg tccctgggca agttttgggt gctggtggtg  1500
gttggtggag tcctggcttg ctatagcttg ctagtaacag tggcctttat tattttctgg  1560
gtgaggagta agaggagcag gctcctgcac agtgactaca tgaacatgac tccccgccgc  1620
cccgggccca cccgcaagca ttaccagccc tatgccccac cacgcgactt cgcagcctat  1680
cgctccaaac ggggcagaaa gaaactcctg tatatattca aacaaccatt tatgagacca  1740
gtacaaacta ctcaagagga agatggctgt agctgccgat ttccagaaga agaagaagga  1800
ggatgtgaac tgagagtgaa gttcagcagg agcgcagacg cccccgcgta caagcagggc  1860
cagaaccagc tctataacga gctcaatcta ggacgaagag aggagtacga tgttttggac  1920
aagagacgtg gccgggaccc tgagatgggg ggaaagccga gaaggaagaa ccctcaggaa  1980
ggcctgtaca atgaactgca gaaagataag atggcggagg cctacagtga gattgggatg  2040
aaaggcgagc gccggagggg caaggggcac gatggccttt accagggtct cagtacagcc  2100
accaaggaca cctacgacgc ccttcacatg caggccctgc cccctcgcta a           2151

SEQ ID NO: 33          moltype = AA  length = 119
FEATURE                Location/Qualifiers
REGION                 1..119
                       note = Heavy chain variable region (VH)
source                 1..119
                       mol_type = protein
                       organism = synthetic construct
SEQUENCE: 33
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 34          moltype = DNA  length = 357
FEATURE                Location/Qualifiers
misc_feature           1..357
                       note = Heavy chain variable region (VH)
source                 1..357
                       mol_type = other DNA
                       organism = synthetic construct
SEQUENCE: 34
caggtgcaat tggtgcagtc tggcgctgaa gttaagaagc ctgggagttc agtgaaggtc  60
tcctgcaagg cttccggata cgccttcagc tattcttgga tcaattgggt gcggcaggcg  120
cctggacaag ggctcgagtg gatgggacgg atctttcccg gcgatgggga tactgactac  180
```

-continued

```
aatgggaaat tcaagggcag agtcacaatt accgccgaca aatccactag cacagcctat  240
atggagctga gcagcctgag atctgaggac acggccgtgt attactgtgc aagaaatgtc  300
tttgatggtt actggcttgt ttactggggc cagggaaccc tggtcaccgt ctcctca     357

SEQ ID NO: 35          moltype = AA  length = 115
FEATURE                Location/Qualifiers
REGION                 1..115
                       note = Light chain variable region (VL)
source                 1..115
                       mol_type = protein
                       organism = synthetic construct
SEQUENCE: 35
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IKRTV       115

SEQ ID NO: 36          moltype = DNA  length = 345
FEATURE                Location/Qualifiers
misc_feature           1..345
                       note = Light chain variable region (VL)
source                 1..345
                       mol_type = other DNA
                       organism = synthetic construct
SEQUENCE: 36
gatatcgtga tgacccagac tccactctcc ctgcccgtca cccctggaga gcccgccagc  60
attagctgca ggtctagcaa gagcctcttg cacagcaatg gcatcactta tttgtattgg  120
tacctgcaaa agccagggca gtctccacag ctcctgattt atcaaatgtc caaccttgtc  180
tctggcgtcc ctgaccggtt ctccggctcc gggtcaggca ctgatttcac actgaaaatc  240
agcagggtgg aggctgagga tgttggagtt tattactgcg ctcagaatct agaacttcct  300
tacaccttcg gcggagggac caaggtggag atcaaacgta cggtg                345

SEQ ID NO: 37          moltype = AA  length = 27
FEATURE                Location/Qualifiers
REGION                 1..27
                       note = Transmembrane domain (TM)
source                 1..27
                       mol_type = protein
                       organism = synthetic construct
SEQUENCE: 37
FWVLVVVGGV LACYSLLVTV AFIIFWV                                     27

SEQ ID NO: 38          moltype = DNA  length = 81
FEATURE                Location/Qualifiers
misc_feature           1..81
                       note = Transmembrane domain (TM)
source                 1..81
                       mol_type = other DNA
                       organism = synthetic construct
SEQUENCE: 38
ttttgggtgc tggtggtggt tggtggagtc ctggcttgct atagcttgct agtaacagtg  60
gcctttatta ttttctgggt g                                           81

SEQ ID NO: 39          moltype = AA  length = 41
FEATURE                Location/Qualifiers
REGION                 1..41
                       note = Co-stimulatory molecule (CS)
source                 1..41
                       mol_type = protein
                       organism = synthetic construct
SEQUENCE: 39
RSKRSRLLHS DYMNMTPRRP GPTRKHYQPY APPRDFAAYR S                     41

SEQ ID NO: 40          moltype = DNA  length = 123
FEATURE                Location/Qualifiers
misc_feature           1..123
                       note = Co-stimulatory molecule (CS)
source                 1..123
                       mol_type = other DNA
                       organism = synthetic construct
SEQUENCE: 40
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                               123
```